US009150841B2

(12) United States Patent
Boldog et al.

(10) Patent No.: US 9,150,841 B2
(45) Date of Patent: *Oct. 6, 2015

(54) CELLS FOR PRODUCING RECOMBINANT IDURONATE-2-SULFATASE

(71) Applicant: Shire Human Genetic Therapies, Inc., Lexington, MA (US)

(72) Inventors: Ferenc Boldog, Lexington, MA (US); Michael Heartlein, Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/829,780

(22) Filed: Mar. 14, 2013

(65) Prior Publication Data
US 2014/0004593 A1  Jan. 2, 2014

Related U.S. Application Data

(60) Provisional application No. 61/666,719, filed on Jun. 29, 2012.

(51) Int. Cl.
*C12N 9/16* (2006.01)

(52) U.S. Cl.
CPC ........................................ *C12N 9/16* (2013.01)

(58) Field of Classification Search
None
See application file for complete search history.

(56) References Cited

U.S. PATENT DOCUMENTS

| | | | |
|---|---|---|---|
| 6,096,555 A | 8/2000 | Hermentin et al. | |
| 6,153,188 A | 11/2000 | Wilson et al. | |
| 6,506,598 B1 | 1/2003 | Andersen et al. | |
| 6,890,736 B1 | 5/2005 | Reddy et al. | |
| 7,083,793 B2 | 8/2006 | Fraser | |
| 7,282,209 B2 | 10/2007 | Fraser | |
| 7,285,398 B2 | 10/2007 | Fraser | |
| 7,323,553 B2 | 1/2008 | Fahrner et al. | |
| 7,368,531 B2 | 5/2008 | Rosen et al. | |
| 7,541,164 B2 | 6/2009 | Schilling et al. | |
| 7,691,611 B2 | 4/2010 | Weber et al. | |
| 8,128,925 B2 | 3/2012 | Vellard et al. | |
| 8,198,084 B2 | 6/2012 | Gorfien et al. | |
| 8,227,212 B2 | 7/2012 | von Figura et al. | |
| 2002/0106358 A1 | 8/2002 | Hopwood et al. | |
| 2011/0318323 A1 | 12/2011 | Zhu et al. | |
| 2013/0028881 A1 | 1/2013 | von Figura et al. | |
| 2014/0004096 A1 | 1/2014 | Nichols | |
| 2014/0004097 A1 | 1/2014 | Zhang et al. | |

FOREIGN PATENT DOCUMENTS

| | | |
|---|---|---|
| JP | 10500939 | 1/1998 |
| JP | 2002017376 | 1/2002 |
| KR | 10-1158673 B1 | 7/2012 |
| WO | WO-89/06279 A1 | 7/1989 |
| WO | WO-00/50443 A2 | 8/2000 |
| WO | WO-01/18022 A1 | 3/2001 |
| WO | WO-01/55411 A2 | 8/2001 |
| WO | WO-01/60991 A2 | 8/2001 |
| WO | WO-01/70804 A1 | 9/2001 |
| WO | WO-01/77137 A1 | 10/2001 |
| WO | WO-02/059327 A2 | 8/2002 |
| WO | WO-02/098455 A2 | 12/2002 |
| WO | WO-2004/072275 A2 | 8/2004 |
| WO | WO-2005/113765 A2 | 12/2005 |
| WO | WO-2011/044542 A1 | 4/2011 |
| WO | WO-2011/163649 A2 | 12/2011 |
| WO | WO-2012/177020 A2 | 12/2012 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession P22304 Aug. 1, 1991.*
Accession Q8NBK3. Jul. 25, 2003.*
International Search Report and Written Opinion for PCT/US13/48601, mailed Dec. 3, 2013.
Chica, R.A. et al., Semi-rational approaches to engineering enzyme activity: combining the benefits of directed evolution and rational design. Current Opinion in Biotechnology, 16(4):378-84 (2005).
Sen, S. et al., Developments in directed evolution for improving enzyme functions, Applied Biochemistry and Biotechnology, 143(3):212-23 (2007).
Abdella et al., A New Cleavable Reagent for Cross-linking and Reversible Immobilization of Proteins, Biochem. Biophys. Res. Commun., 87(3):734-742 (1979).
Benjdia et al., First evidences for a third sulfatase maturation system in prokaryotes from *E. coli* asiB and ydeM deletion mutants, FEBS Letters, 581:1009-1014 (2007).
Bielicki et al., H
Bielicki, J. et al., Expression, purification and characterization of recombinant human N-acetylgalactosaminea-6-sulphatase, Biochem. J., 311:333-339, 1995.
Cosma et al., "The Multiple Sulfatase Deficiency Gene Encodes an Essential and Limiting Factor for the Activity of Sulfatases", Cell, 113:445-456 (2003).
Database EMBL, Database Accession No. AAAB01008987 (Jul. 24, 2002).
Database EMBL, Database Accession No. AAB88402 (May 23, 2001).
Database EMBL, Database Accession No. AAY95971 (Dec. 5, 2000). uman liver iduronate-2-sulphatase, Biochem. J., 271:75-86 (1990).
Bielicki, et al., Human liver iduronate-2-sulphatase, Biochem. J., 271:75-86 (1990).

(Continued)

*Primary Examiner* — Christian Fronda
(74) *Attorney, Agent, or Firm* — Choate, Hall & Stewart LLP

(57) ABSTRACT

The present invention provides, among other things, methods and compositions for production of recombinant I2S protein with improved potency and activity using cells co-express I2S and FGE protein. In some embodiments, cells according to the present invention are engineered to simultaneously overexpress recombinant I2S and FGE proteins. Cells according to the invention are adaptable to various cell culture conditions. In some embodiments, cells of the present invention adaptable to a large-scale suspension serum-free culture.

22 Claims, 5 Drawing Sheets

(56) References Cited

OTHER PUBLICATIONS

Database EMBL, Database Accession No. P95060 (May 1, 1997).
Database EMBL, Database Accession No. Q7V5N5 (Oct. 1, 2003).
Database EMBL, Database Accession No. Q88HK3 (Jun. 1, 2003).
Database EMBL, Database Accession No. Q8FTJ8 (Mar. 1, 2003).
Database EMBL, Database Accession No. Q92WL9 (Dec. 1, 2001).
Database EMBL, Database Accession No. Q93PA2 (Dec. 1, 2001).
Database EMBL, Database Accession No. Q9A921 (Jun. 1, 2001).
Database EMBL, Database Accession No. Q9F3C7 (Mar. 1, 2001).
Database EMBL, Database Accession No. ABB62912 (Mar. 26, 2002).
Database EMBL, Database Accession No. AK076022 (Dec. 13, 2002).
Database EMBL, Database Accession No. BD551115 (Sep. 18, 2002).
Database EMBL, Database Accession No. Q98BQ8 (Oct. 1, 2001).
Dierks et al., "Multiple Sulfatase Deficiency is Caused by Mutations in the Gene Encoding the Human Ca-Formylglycine Generating Enzyme", Cell, 113(4):435-444 (2003).
Dierks et al., "Sequence determinants directing conversion of cysteine to formylglycine in eukaryotic sulfatases", The EMBO J., 18(8):2084-2091 (1999).
Dierks et al., Conversion of cysteine to formylglycine: A protein modification in the endoplasmic reticulum, Proc. Natl. Acad. Sci. USA, 94:11963-11968 (1997).
Eto et al., "Multiple Sulfatase Deficiency (Mucosulfatidosis): Impaired Degradation of Labeled Sulfated Compounds in Cultured Skin Fibroblasts in vivo", Eur. J. Pediatr., 135:85-89 (1980).
Fang et al., "Post-translational Formylglycine Modification of Bacterial Sulfatases by the Radical S-Adenosylmethionine Protein AtsB", J. Bioi. Chem., 279(15):14570-14578 (2004).
Ferrante, P. et al., Molecular and biochemical characterisatin of a novel sulphatase gene: Arylsulfatase G (ARSG), Eur. J. Hum. Genet., 10(12):813-818, 2002.
Fey et al., "Characterization of Posttranslational Formylglycine Formation by Luminal Components of the Endoplasmic Reticulum", 276(50):47021-47028 (2001).
GenBank Accession No. AJ131525 (Apr. 14, 1999).
Juengst, E. T., "What next for human gene therapy?", BMJ, 326:1410-1411 (2003).
Knaust et al., Residues Critical for Formylglycine Formation and/or Catalytic Activity of Arylsulfatase A, Biochemistry, 37:13941-13946 (1998).
Landgrebe et al., "The human SUMF1 gene, required for post-translational sulfatase modification, defines a new gene family which is conserved from pro- to eukaryotes", Gene, 316:47-56 (2003).
Merriam-Webster online dictionary definition of "exogenous", obtained from www.merriam-webster.com/dictionary/exogenous, last viewed on Aug. 4, 2010 (1 page).
Merriam-Webster online dictionary definition of "exogenous", obtained from www.merriam-webster.com/dictionary/exogenous, last viewed on Dec. 18, 2009 (2 pages).
Morimoto-Tomita, M. et al., Cloning and Characterization of Two Extracellular Heparin-degrading Endosulfatase in Mice and Humans, J. Biol. Chem., 277(51):49175-49185, (2002).
Plasmid Vectors, obtained from WININ.mfa.od.ua/page275.htm, last viewed on May 9, 2011 (2 pages).
Rommerskirch et al., "Multiple sulfatase deficiency: Catalytically inductive sulfatases are expressed from retrovirally introduced sulfatase cDNAs", PNAS, 89:2561-2565 (1992).
Sang, H., "Prospects for transgenesis in the chick", Mechanisms of Development, 121:1179-1186 (2004).
Schirmer et al., "Computational analysis of bacterial sulfatases and their modifying enzymes", Chem. Bioi., 5(8):R181-R186 (1998).
Schmidt et al., "A Novel Amino Acid Modification in Sulfatases that is Defective in Multiple Sulfatase Deficiency", Cell, 82(2):271-278 (1995).
Szameit et al., "The Iron Sulfur Protein AtsB is Required for Post-translational Formation of Formylglycine in the *Klebsiella* Sulfatase", J. Bioi. Chem., 274(22):15375-15381 (1999).
Tomaisu, S., Morquio Disease: Isolation, Characterization and Expression of Full-Length cDNA for Human N-Acetylgalactosamine-6-Sulfate Sulfatase, Biocehm. Biophys. Res. Commun., 181(2):677-683, 1991.
Wraith et al., "The clinical phenotype of two patients with a complete deletion of the iduronate-2-sulphatase gene (mucopolysaccharidosis II—Hunter syndrome)", Hum. Genet., 87:205-206 (1991).
International Search Report and Written Opinion for PCT/US13/48561, mailed Dec. 12, 2013.
International Search Report and Written Opinion for PCT/US13/48571, mailed Dec. 12, 2013.
Bielicki, J. et al., Recombinant human iduronate-2-sulphatase: correction of mucopolysaccharidosis-type II fibroblasts and characterization of the purified enzyme, Journal of Biochemistry, 289: 241-256 (1993).
Burgess, Richard R., Protein Purification, Proteomics of the Nervous System, 1-18 (2008).
Rivera-Colon, Y. et al., The Structure of Human Galns Reveals the Molecular Basis for Mucopolysaccharidosis IV A, Journal of Molecular Biology, 423:736-751 (2012).
U.S. Department of Health and Human Services, Food and Drug Administration, Guidance for Industry, Scientific Consideration in Demonstrating Biosimilarity to a Reference Product, 1-22 (Feb. 2012).

* cited by examiner

SEQ ID NO: 1

| | | | | | | | | | | |
|---|---|---|---|---|---|---|---|---|---|---|
| 1 | Ser | Glu | Thr | Gln | Ala | Asn | Ser | Thr | Asp | Ala | Leu | Asn | Val | Leu | Leu | Ile | Ile | Val | Asp |
| 21 | Asp | Leu | Arg | Pro | Ser | Leu | Gly | Cys | Tyr | Gly | Asp | Lys | Leu | Val | Arg | Ser | Pro | Asn | Ile | Asp |
| 41 | Gln | Leu | Ala | Ser | His | Ser | Leu | Leu | Phe | Gln | Asn | Ala | Phe | Ala | Gln | Ala | Val | Cys | Ala |
| 61 | Pro | Ser | Arg | Bal | Ser | Phe | Ser | Leu | Thr | Gly | Arg | Arg | Arg | Pro | Asp | Thr | Arg | Leu | Tyr | Asp | Phe |
| 81 | Asn | Ser | Tyr | Trp | Arg | Val | His | Ala | Gly | Asn | Phe | Ser | Thr | Ile | Pro | Gln | Tyr | Phe | Lys | Glu |
| 101 | Asn | Gly | Tyr | Val | Thr | Met | Ser | Val | Gly | Lys | Val | Phe | His | Pro | Gly | Ile | Ser | Ser | Asn | His |
| 121 | Thr | Asp | Asp | Ser | Pro | Tyr | Ser | Trp | Ser | Phe | Pro | Pro | Tyr | His | Pro | Ser | Ser | Glu | Lys | Tyr |
| 141 | Glu | Asn | Thr | Lys | Cys | Arg | Gly | Pro | Asp | Gly | Thr | Leu | Pro | Asp | Lys | Gln | Leu | His | Ala | Asn | Leu | Leu | Cys | Pro |
| 161 | Val | Asp | Val | Leu | Asp | Val | Pro | Glu | Gly | Thr | Leu | Pro | Asp | Lys | Ala | Ser | Pro | Phe | Leu | Ala | Val | Gly | Ala |
| 181 | Ile | Gln | Leu | Leu | Glu | Lys | Met | Lys | Pro | Gly | Val | Phe | Arg | Tyr | Pro | Lys | Ala | Ser | Pro | Phe | Leu | Ala | Val | Gly | Ala |
| 201 | His | Lys | Pro | His | Ile | Pro | Phe | Arg | Tyr | Pro | Lys | Glu | Phe | Gln | Phe | Gln | Lys | Leu | Tyr | Pro | Leu | Glu |
| 221 | Asn | Ile | Thr | Leu | Ala | Pro | Asp | Gly | Val | Pro | Val | Gln | Ala | Leu | Asn | Ile | Ser | Val | Pro | Tyr |
| 241 | Pro | Trp | Met | Asp | Ile | Arg | Gln | Arg | Glu | Asp | Val | Gln | Ala | Val | Gln | Ser | Gln | Ala | Tyr | Asn |
| 261 | Gly | Pro | Ile | Pro | Val | Asp | Phe | Gln | Arg | Lys | Ile | Arg | Gln | Ser | Tyr | Phe | Ala | Ser | Val | Ser |

FIG. 1A

```
281  Tyr Leu Asp Thr Gln Val Gly Arg Leu Leu Ser Ala Leu Asp Asp Leu Gln Leu Ala Asn
301  Ser Thr Ile Ile Ala Phe Thr Ser Asp His Gly Trp Ala Leu Gly Glu His Gly Glu Trp
321  Ala Lys Tyr Ser Asn Phe Asp Val Ala Thr His Val Pro Leu Ile Phe Tyr Val Pro Gly
341  Arg Thr Ala Ser Leu Pro Glu Ala Gly Glu Lys Leu Phe Pro Tyr Leu Asp Pro Phe Asp
361  Ser Ala Ser Gln Leu Met Glu Pro Gly Arg Gln Ser Met Asp Leu Val Glu Leu Val Ser
381  Leu Phe Pro Thr Leu Ala Gly Leu Ala Gly Leu Gln Val Pro Arg Cys Pro Val Pro
401  Ser Phe His Val Glu Leu Cys Arg Glu Gly Lys Asn Leu Leu Lys His Phe Arg Phe Arg
421  Asp Leu Glu Asp Pro Tyr Leu Pro Gly Asn Pro Arg Glu Leu Ile Ala Tyr Ser Gln
441  Tyr Pro Arg Pro Ser Asp Ile Pro Gln Trp Asn Ser Asp Lys Pro Ser Leu Lys Asp Ile
461  Lys Ile Met Gly Tyr Ser Ile Arg Thr Ile Asp Tyr Arg Tyr Thr Val Trp Val Gly Phe
481  Asn Pro Asp Glu Phe Leu Ala Asn Phe Ser Asp Ile His Ala Gly Glu Leu Tyr Phe Val
501  Asp Ser Asp Pro Leu Gln Asp His Asn Met Tyr Asn Asp Ser Gln Gly Gly Asp Leu Phe
521  Gln Leu Leu Met Pro
```

Asn - marks sites of N-linked glycosylation
Cys - example site of cysteine conversion

FIG. 1B

FIG. 2A
I2S and SUMF1 co-expression options
Expression units on separate vectors (co-transfection or subsequent transfections)
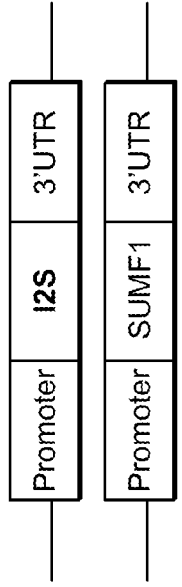
FIG. 2B
Expression units on the same vector (one transfection)
1) Separate cistrons
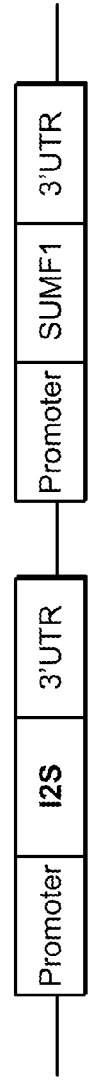
2) Transcriptionally linked cistrons
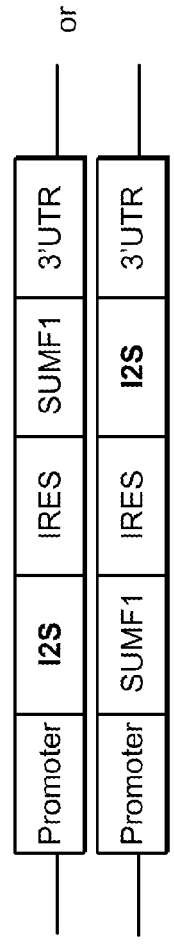
or

SEQUENCE LISTING

<160> NUMBER OF SEQ ID NOS: 8

<210> SEQ ID NO 1
<211> LENGTH: 525
<212> TYPE: PRT
<213> ORGANISM: Homo sapiens

<400> SEQUENCE: 1

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95
```

```
Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
            130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510
```

```
Asp Ser Gln Gly Gly Asp Leu Phe Gln Leu Leu Met Pro
            515                 520                 525
```

```
<210> SEQ ID NO 2
<211> LENGTH: 550
<212> TYPE: PRT
<213> ORGANISM: Homo sapiens

<400> SEQUENCE: 2

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365
```

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550

<210> SEQ ID NO 3
<211> LENGTH: 312
<212> TYPE: PRT
<213> ORGANISM: Homo sapiens

<400> SEQUENCE: 3

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro

```
            180                 185                 190
Glu Gly Thr Leu Pro Asp Lys Gln Ser Thr Glu Gln Ala Ile Gln Leu
            195                 200                 205

Leu Glu Lys Met Lys Thr Ser Ala Ser Pro Phe Phe Leu Ala Val Gly
            210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
            275                 280                 285

Pro Val Asp Phe Gln Glu Asp Gln Ser Ser Thr Gly Phe Arg Leu Lys
            290                 295                 300

Thr Ser Ser Thr Arg Lys Tyr Lys
305                 310

<210> SEQ ID NO 4
<211> LENGTH: 343
<212> TYPE: PRT
<213> ORGANISM: Homo sapiens

<400> SEQUENCE: 4

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
            210                 215                 220

Tyr His Lys Pro His Ile Pro Phe Arg Tyr Pro Lys Glu Phe Gln Lys
225                 230                 235                 240
```

```
Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Phe Leu Met Arg Thr Asn Thr
                340

<210> SEQ ID NO 5
<211> LENGTH: 341
<212> TYPE: PRT
<213> ORGANISM: Homo sapiens

<400> SEQUENCE: 5

Ser Gln Glu Ala Gly Thr Gly Ala Gly Ala Gly Ser Leu Ala Gly Ser
1               5                   10                  15

Cys Gly Cys Gly Thr Pro Gln Arg Pro Gly Ala His Gly Ser Ser Ala
            20                  25                  30

Ala Ala His Arg Tyr Ser Arg Glu Ala Asn Ala Pro Gly Pro Val Pro
        35                  40                  45

Gly Glu Arg Gln Leu Ala His Ser Lys Met Val Pro Ile Pro Ala Gly
    50                  55                  60

Val Phe Thr Met Gly Thr Asp Asp Pro Gln Ile Lys Gln Asp Gly Glu
65                  70                  75                  80

Ala Pro Ala Arg Arg Val Thr Ile Asp Ala Phe Tyr Met Asp Ala Tyr
                85                  90                  95

Glu Val Ser Asn Thr Glu Phe Glu Lys Phe Val Asn Ser Thr Gly Tyr
            100                 105                 110

Leu Thr Glu Ala Glu Lys Phe Gly Asp Ser Phe Val Phe Glu Gly Met
        115                 120                 125

Leu Ser Glu Gln Val Lys Thr Asn Ile Gln Gln Ala Val Ala Ala Ala
    130                 135                 140

Pro Trp Trp Leu Pro Val Lys Gly Ala Asn Trp Arg His Pro Glu Gly
145                 150                 155                 160

Pro Asp Ser Thr Ile Leu His Arg Pro Asp His Pro Val Leu His Val
                165                 170                 175

Ser Trp Asn Asp Ala Val Ala Tyr Cys Thr Trp Ala Gly Lys Arg Leu
            180                 185                 190

Pro Thr Glu Ala Glu Trp Glu Tyr Ser Cys Arg Gly Gly Leu His Asn
        195                 200                 205

Arg Leu Phe Pro Trp Gly Asn Lys Leu Gln Pro Lys Gly Gln His Tyr
    210                 215                 220

Ala Asn Ile Trp Gln Gly Glu Phe Pro Val Thr Asn Thr Gly Glu Asp
225                 230                 235                 240

Gly Phe Gln Gly Thr Ala Pro Val Asp Ala Phe Pro Pro Asn Gly Tyr
                245                 250                 255

Gly Leu Tyr Asn Ile Val Gly Asn Ala Trp Glu Trp Thr Ser Asp Trp
            260                 265                 270
```

Trp Thr Val His His Ser Val Glu Glu Thr Leu Asn Pro Lys Gly Pro
            275                 280                 285

Pro Ser Gly Lys Asp Arg Val Lys Lys Gly Gly Ser Tyr Met Cys His
    290                 295                 300

Arg Ser Tyr Cys Tyr Arg Tyr Arg Cys Ala Ala Arg Ser Gln Asn Thr
305                 310                 315                 320

Pro Asp Ser Ser Ala Ser Asn Leu Gly Phe Arg Cys Ala Ala Asp Arg
                325                 330                 335

Leu Pro Thr Met Asp
            340

<210> SEQ ID NO 6
<211> LENGTH: 374
<212> TYPE: PRT
<213> ORGANISM: Homo sapiens

<400> SEQUENCE: 6

Met Ala Ala Pro Ala Leu Gly Leu Val Cys Gly Arg Cys Pro Glu Leu
1               5                   10                  15

Gly Leu Val Leu Leu Leu Leu Leu Ser Leu Leu Cys Gly Ala Ala
            20                  25                  30

Gly Ser Gln Glu Ala Gly Thr Gly Ala Gly Ala Gly Ser Leu Ala Gly
            35                  40                  45

Ser Cys Gly Cys Gly Thr Pro Gln Arg Pro Gly Ala His Gly Ser Ser
    50                  55                  60

Ala Ala Ala His Arg Tyr Ser Arg Glu Ala Asn Ala Pro Gly Pro Val
65                  70                  75                  80

Pro Gly Glu Arg Gln Leu Ala His Ser Lys Met Val Pro Ile Pro Ala
                85                  90                  95

Gly Val Phe Thr Met Gly Thr Asp Asp Pro Gln Ile Lys Gln Asp Gly
            100                 105                 110

Glu Ala Pro Ala Arg Arg Val Thr Ile Asp Ala Phe Tyr Met Asp Ala
            115                 120                 125

Tyr Glu Val Ser Asn Thr Glu Phe Glu Lys Phe Val Asn Ser Thr Gly
    130                 135                 140

Tyr Leu Thr Glu Ala Glu Lys Phe Gly Asp Ser Phe Val Phe Glu Gly
145                 150                 155                 160

Met Leu Ser Glu Gln Val Lys Thr Asn Ile Gln Gln Ala Val Ala Ala
                165                 170                 175

Ala Pro Trp Trp Leu Pro Val Lys Gly Ala Asn Trp Arg His Pro Glu
            180                 185                 190

Gly Pro Asp Ser Thr Ile Leu His Arg Pro Asp His Pro Val Leu His
            195                 200                 205

Val Ser Trp Asn Asp Ala Val Ala Tyr Cys Thr Trp Ala Gly Lys Arg
    210                 215                 220

Leu Pro Thr Glu Ala Glu Trp Glu Tyr Ser Cys Arg Gly Gly Leu His
225                 230                 235                 240

Asn Arg Leu Phe Pro Trp Gly Asn Lys Leu Gln Pro Lys Gly Gln His
                245                 250                 255

Tyr Ala Asn Ile Trp Gln Gly Glu Phe Pro Val Thr Asn Thr Gly Glu
            260                 265                 270

Asp Gly Phe Gln Gly Thr Ala Pro Val Asp Ala Phe Pro Pro Asn Gly
            275                 280                 285

Tyr Gly Leu Tyr Asn Ile Val Gly Asn Ala Trp Glu Trp Thr Ser Asp

```
                290                  295                  300
Trp Trp Thr Val His His Ser Val Glu Glu Thr Leu Asn Pro Lys Gly
305                 310                  315                  320

Pro Pro Ser Gly Lys Asp Arg Val Lys Lys Gly Gly Ser Tyr Met Cys
                325                  330                  335

His Arg Ser Tyr Cys Tyr Arg Tyr Arg Cys Ala Ala Arg Ser Gln Asn
                340                  345                  350

Thr Pro Asp Ser Ser Ala Ser Asn Leu Gly Phe Arg Cys Ala Ala Asp
            355                  360                  365

Arg Leu Pro Thr Met Asp
        370

<210> SEQ ID NO 7
<211> LENGTH: 1653
<212> TYPE: DNA
<213> ORGANISM: Homo sapiens

<400> SEQUENCE: 7 atgccccgc cccgcaccgg ccgcggcctg ctgtggctgg gcctggtgct gagcagcgtg      60
tgcgtggccc tgggcagcga gacccaggcc aacagcacca ccgacgccct gaacgtgctg    120
ctgatcatcg tggacgacct cgccccagc ctgggctgct acggcgacaa gctggtgcgc    180
agccccaaca tcgaccagct ggccagccac agcctgctgt ccagaacgc cttcgcccag    240
caggccgtgt gcgcccccag ccgcgtgagc ttcctgaccg gccgccgccc cgacaccacc    300
cgcctgtacg acttcaacag ctactggcgc gtgcacgccg gcaacttcag caccatcccc    360
cagtacttca aggagaacgg ctacgtgacc atgagcgtgg gcaaggtgtt ccaccccggc    420
atcagcagca ccacaccga cagcccc tacagctgga gcttcccccc ctaccacccc        480
agcagcgaga gtacgagaa caccaagacc tgccgcggcc ccgacggcga gctgcacgcc    540
aacctgctgt gccccgtgga cgtgctggac gtgcccgagg caccctgcc cgacaagcag    600
agcaccgagc aggccatcca gctgctggag aagatgaaga ccagcgccag cccttcttc    660
ctggccgtgg gctaccacaa gccccacatc cccttccgct accccaagga gttccagaag    720
ctgtaccccc tggagaacat cacctggcc ccgaccccga ggtgcccga cggcctgccc    780
ccgtggcct acaaccctg gatggacatc cgccagcgcg aggacgtgca ggccctgaac    840
atcagcgtgc cctacggccc catccccgtg acttccagc gcaagatccg ccagagctac    900
ttcgccagcg tgagctacct ggacacccag gtgggccgcc tgctgagcgc cctggacgac    960
ctgcagctgg ccaacagcac catcatcgcc ttcaccagcg accacggctg ggcctgggc   1020
gagcacggcg agtgggccaa gtacagcaac ttcgacgtgg ccacccacgt gccctgatc   1080
ttctacgtgc ccgccgcac cgccagcctg cccgaggccg cgagaagct gttcccctac   1140
ctggacccct cgacagcgc cagccagctg atggagcccg ccgccagag catggacctg   1200
gtggagctgt gagcctgtt ccccaccctg gccggcctgg ccggcctgca ggtgccccc   1260
cgctgccccg tgcccagctt ccacgtggag ctgtgccgcg agggcaagaa cctgctgaag   1320
cacttccgct ccgcgacct ggaggaggac ccctacctgc ccggcaaccc cgcgagctg    1380
atcgcctaca gccagtaccc ccgccccagc gacatccccc agtggaacag cgacaagccc   1440
agcctgaagg acatcaagat catgggctac agcatccgca ccatcgacta ccgctacacc   1500
gtgtgggtgg gcttcaaccc cgacgagttc ctggccaact tcagcgacat ccacgccggc   1560
gagctgtact tcgtggacag cgaccccctg caggaccaca acatgtacaa cgacagccag   1620
```

```
ggcggcgacc tgttccagct gctgatgccc tag                         1653
```

<210> SEQ ID NO 8
<211> LENGTH: 1125
<212> TYPE: DNA
<213> ORGANISM: Homo sapiens

<400> SEQUENCE: 8

```
atggctgcgc ccgcactagg gctggtgtgt ggacgttgcc ctgagctggg tctcgtcctc    60
ttgctgctgc tgctctcgct gctgtgtgga gcggcaggga gccaggaggc cgggaccggt   120
gcgggcgcgg ggtccttgc gggttcttgc ggctgcggca cgcccagcg gcctggcgcc    180
catggcagtt cggcagccgc tcaccgatac tcgcgggagg ctaacgctcc gggccccgta   240
cccggagagc ggcaactcgc gcactcaaag atggtcccca tccctgctgg agtatttaca   300
atgggcacag atgatcctca gataaagcag gatggggaag cacctgcgag gagagttact   360
attgatgcct tttacatgga tgcctatgaa gtcagtaata ctgaatttga gaagtttgtg   420
aactcaactg gctatttgac agaggctgag aagtttggcg actcctttgt ctttgaaggc   480
atgttgagtg agcaagtgaa gaccaatatt caacaggcag ttgcagctgc tccctggtgg   540
ttacctgtga aaggcgctaa ctggagacac ccagaagggc ctgactctac tattctgcac   600
aggccggatc atccagttct ccatgtgtcc tggaatgatg cggttgccta ctgcacttgg   660
gcagggaagc ggctgcccac ggaagctgag tgggaataca gctgtcgagg aggcctgcat   720
aatagacttt tcccctgggg caacaaactg cagcccaaag gccagcatta tgccaacatt   780
tggcagggcg agtttccggt gaccaacact ggtgaggatg gcttccaagg aactgcgcct   840
gttgatgcct tccctcccaa tggttatggc ttatacaaca tagtggggaa cgcatgggaa   900
tggacttcag actggtggac tgttcatcat tctgttgaag aaacgcttaa cccaaaaggt   960
cccccttctg ggaaagaccg agtgaagaaa ggtggatcct acatgtgcca taggtcttat  1020
tgttacaggt atcgctgtgc tgctcggagc cagaacacac ctgatagctc tgcttcgaat  1080
ctgggattcc gctgtgcagc cgaccgcctg cccaccatgg actga                  1125
```

CELLS FOR PRODUCING RECOMBINANT IDURONATE-2-SULFATASE

CROSS REFERENCE TO RELATED APPLICATIONS

This application claims benefit under 35 USC §119(e) of U.S. Provisional Patent Application Ser. No. 61/666,719, filed Jun. 29, 2012, which application is hereby incorporated by reference in its entirety.

SEQUENCE LISTING

The present specification makes reference to a Sequence Listing submitted in electronic form as an ASCII.txt file named "2006685-0277_SEQ_LIST" on Mar. 14, 2013. The .txt file was generated on Mar. 5, 2013 and is 25 KB in size. The entire contents of the Sequence Listing are herein incorporated by reference.

BACKGROUND

Mucopolysaccharidosis type II (MPS II, Hunter syndrome) is an X-chromosome-linked recessive lysosomal storage disorder that results from a deficiency in the enzyme iduronate-2-sulfatase (I2S). I2S cleaves the terminal 2-O-sulfate moieties from the glycosaminoglycans (GAG) dermatan sulfate and heparan sulfate. Due to the missing or defective I2S enzyme in patients with Hunter syndrome, GAG progressively accumulate in the lysosomes of a variety of cell types, leading to cellular engorgement, organomegaly, tissue destruction, and organ system dysfunction.

Generally, physical manifestations for people with Hunter syndrome include both somatic and neuronal symptoms. For example, in some cases of Hunter syndrome, central nervous system involvement leads to developmental delays and nervous system problems. While the non-neuronal symptoms of Hunter Syndrome are generally absent at birth, over time the progressive accumulation of GAG in the cells of the body can have a dramatic impact on the peripheral tissues of the body. GAG accumulation in the peripheral tissue leads to a distinctive coarseness in the facial features of a patient and is responsible for the prominent forehead, flattened bridge and enlarged tongue, the defining hallmarks of a Hunter patient. Similarly, the accumulation of GAG can adversely affect the organ systems of the body. Manifesting initially as a thickening of the wall of the heart, lungs and airways, and abnormal enlargement of the liver, spleen and kidneys, these profound changes can ultimately lead to widespread catastrophic organ failure. As a result, Hunter syndrome is always severe, progressive, and life-limiting.

Enzyme replacement therapy (ERT) is an approved therapy for treating Hunter syndrome (MPS II), which involves administering exogenous replacement I2S enzyme to patients with Hunter syndrome.

SUMMARY OF THE INVENTION

The present invention provides, among other things, improved methods and compositions for production of recombinant I2S protein that allows more effective enzyme replacement therapy for Hunter syndrome. The present invention encompasses the discovery that more potent recombinant I2S protein can be produced by mammalian cells engineered to co-express a recombinant I2S protein and a formylglycine generating enzyme (FGE). Unexpectedly, recombinant I2S protein produced by such engineered cells has an unusually high level of $C_\alpha$, formylglycine (FGly) conversion percentage (e.g., greater than 70% and up to 100%), resulting in significantly improved enzymatic activity of recombinant I2S protein. In addition, mammalian cells co-expressing I2S and FGE proteins according to the present invention have been successfully adapted to grow in suspension culture at a large scale. Therefore, the present invention allows more efficient large scale production of highly potent recombinant I2S protein.

Thus, in one aspect, the present invention provides a cell containing a first nucleic acid encoding an iduronate-2-sulfatase (I2S) protein having an amino acid sequence at least about 50% (e.g., at least about 55%, 60%, 65%, 70%, 75%, 80%, 85%, 90%, 95%, 96%, 97%, 98%, or 99%) identical to SEQ ID NO:1; and a second nucleic acid encoding a formylglycine generating enzyme (FGE) protein comprising an amino acid sequence at least about 50% (e.g., at least about 55%, 60%, 65%, 70%, 75%, 80%, 85%, 90%, 95%, 96%, 97%, 98%, or 99%) identical to SEQ ID NO:5, wherein the first and/or the second nucleic acid are exogenous and wherein the cell, once cultivated under a cell culture condition (e.g., suspension or adherent culture), produces the I2S protein comprising at least about 70% (e.g., at least about 75%, 80%, 85%, 90%, 95%, 96%, 97%, 98%, 99%, or 100%) conversion of the cysteine residue corresponding to Cys59 of SEQ ID NO:1 to Cα-formylglycine (FGly).

In another aspect, the present invention provides a cell containing a first nucleic acid encoding an iduronate-2-sulfatase (I2S) protein having an amino acid sequence at least about 50% (e.g., at least about 55%, 60%, 65%, 70%, 75%, 80%, 85%, 90%, 95%, 96%, 97%, 98%, or 99%) identical to SEQ ID NO:1; and a second nucleic acid encoding a formylglycine generating enzyme (FGE) protein comprising an amino acid sequence at least about 50% (e.g., at least about 55%, 60%, 65%, 70%, 75%, 80%, 85%, 90%, 95%, 96%, 97%, 98%, or 99%) identical to SEQ ID NO:5, wherein the first and/or the second nucleic acid are exogenous and wherein the cell, once cultivated under a cell culture condition, produces I2S protein comprising at least about 50% (e.g., at least about 55%, 60%, 65%, 70%, 75%, 80%, 85%, 90%, 95%, 96%, 97%, 98%, 99%, or 100%) conversion of the cysteine residue corresponding to Cys59 of SEQ ID NO:1 to Cα-formylglycine (FGly) and at a specific productivity rate of great than about 10 picogram/cell/day (e.g., greater than about 15, 20, 25, 30, 35, 40, 45, 50, 55, 60, 65, 70, 75, 80, 85, 90, 95, or 100 picogram/cell/day).

In some embodiments, the first nucleic acid encodes an I2S protein having an amino acid sequence identical to SEQ ID NO:1. In some embodiments, the second nucleic acid encodes an FGE protein having an amino acid sequence identical to SEQ ID NO:5.

In some embodiments, the first and/or the second nucleic acid is operably linked to a hCMV promoter.

In some embodiments, the first and/or second nucleic acid are codon optimized. In some embodiments, the first nucleic acid has a sequence at least about 50% (e.g., at least about 55%, 60%, 65%, 70%, 75%, 80%, 85%, 90%, 95%, 96%, 97%, 98%, 99%) identical to SEQ ID NO:7. In particular embodiments, the first nucleic acid has a sequence of SEQ ID NO:7.

In some embodiments, the second nucleic acid comprises a sequence at least about 50% (e.g., at least about 55%, 60%, 65%, 70%, 75%, 80%, 85%, 90%, 95%, 96%, 97%, 98%, 99%) identical to SEQ ID NO:8. In some embodiments, the second nucleic acid has a sequence identical to SEQ ID NO:8.

In some embodiments, both of the first and second nucleic acids are exogenous (also referred to as recombinant). In some embodiments, the first and/or second nucleic acids are integrated (e.g., stably) in the genome of the cell. In some embodiments, the first and/or second nucleic acids are present in one or more extra-chromosomal constructs.

In some embodiments, a cell of the present invention is a mammalian cell. In certain embodiments, a suitable mammalian cell is a human cell. In certain embodiments, a suitable mammalian cell is a CHO cell.

In some embodiments, a cell according to the invention is adaptable to suspension culture. In other embodiments, a cell according to the invention is adherent.

In a further aspect, the present invention provides a method of producing recombinant iduronate-2-sulfatase (I2S) protein by cultivating a cell described in various embodiments herein under conditions such that the recombinant I2S and FGE proteins are co-expressed in the cell. In some embodiments, the cell is cultivated at a large scale. In some embodiments, a large scale suitable for the present invention is a bioreactor process. In some embodiments, a bioreactor suitable for the invention is at a scale selected from 10 L, 200 L, 500 L, 1000 L, 1500 L, 2000 L. In some embodiments, a large scale (e.g., bioreactor) process suitable for the present invention involves a perfusion process. In some embodiments, a large scale (e.g., bioreactor) process suitable for the present invention involves a batch culture. In some embodiments, a large scale process suitable for the present invention is a roller bottle process. In some embodiments, a cell according to the present invention is cultivated in suspension. In other embodiments, a cell according to the present invention is cultivated adherent.

In some embodiments, a cell according to the present invention is cultivated in a serum-free medium (e.g., animal-free, chemically-defined, or protein-free medium). In other embodiments, a cell according to the present invention is cultivated in a serum-containing medium.

In various embodiments, a method according to the invention further includes a step of purifying the recombinant I2S protein.

In still another aspect, the present invention provides a recombinant iduronate-2-sulfatase (I2S) protein produced by a cell or method described in various embodiments herein.

In some embodiments, the present invention provides a preparation of recombinant iduronate-2-sulfatase (I2S) protein, in which said recombinant I2S protein has an amino acid sequence at least about 50% (e.g., at least about 55%, 60%, 65%, 70%, 75%, 80%, 85%, 90%, 95%, 96%, 97%, 98%, 99%) identical to SEQ ID NO:1; and containing at least about 70% (e.g., at least about 75%, 80%, 85%, 90%, 95%, 96%, 97%, 98%, 99%, 100%) conversion of the cysteine residue corresponding to Cys59 of SEQ ID NO:1 to $C_\alpha$-formylglycine (FGly). In some embodiments, the recombinant I2S protein has an amino acid sequence identical to SEQ ID NO:1. In some embodiments, the recombinant I2S protein has specific activity of at least about 20 U/mg, 30 U/mg, 40 U/mg, 50 U/mg, 60 U/mg, 70 U/mg, 80 U/mg, 90 U/mg, or 100 U/mg as determined by an in vitro sulfate release activity assay using heparin disaccharide as substrate.

Among other things, the present invention also provides a pharmaceutical composition containing a recombinant I2S protein described in various embodiments herein and a pharmaceutically acceptable carrier and a method of treating Hunter syndrome by administering into a subject in need of treatment recombinant I2S protein described herein or a pharmaceutical composition containing the same.

As used herein, the terms "I2S protein," "I2S," "I2S enzyme," or grammatical equivalents, refer to a preparation of recombinant I2S protein molecules unless otherwise specifically indicated.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The Figures described below, that together make up the Drawings, are for illustration purposes only, not for limitation.

FIG. 1 depicts the amino acid sequence encoding the mature form of human iduronate-2-sulfatase (I2S) protein and indicates potential sites within the protein sequence for N-linked glycosylation and cysteine conversion.

FIG. 2 depicts exemplary construct designs for co-expression of I2S and FGE (i.e., SUMF1). (A) Expression units on separate vectors (for co-transfection or subsequent transfections); (B) Expression units on the same vector (one transfection): (1) Separate cistrons and (2) Transcriptionally linked cistrons.

DEFINITIONS

Figure 3:
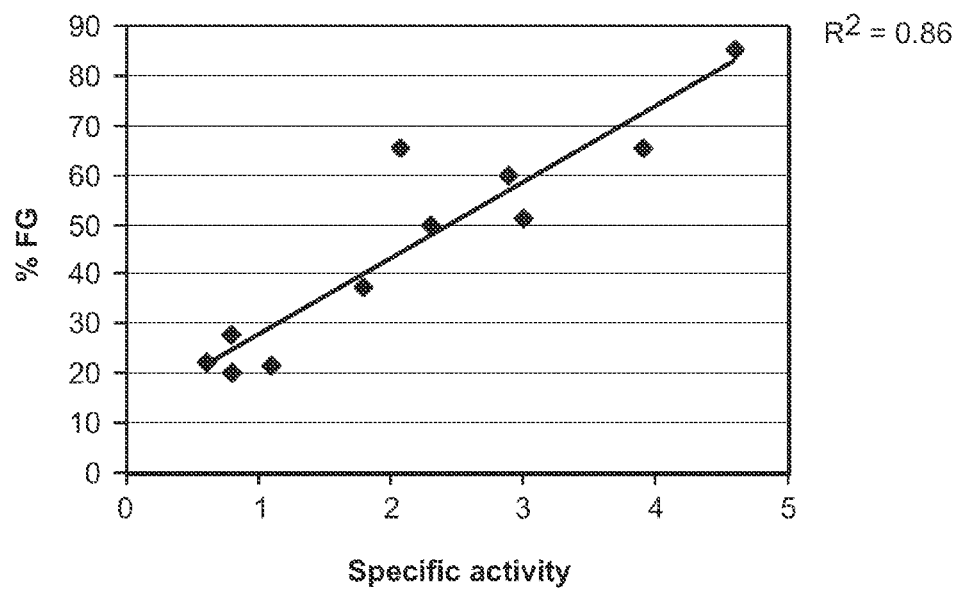
FIG. 3 depicts exemplary levels of I2S specific activity observed as correlated to percent formylglycine conversion.

In order for the present invention to be more readily understood, certain terms are first defined. Additional definitions for the following terms and other terms are set forth throughout the specification.

Amino acid: As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc. In some embodiments, amino acids of the present invention may be provided in or used to supplement medium for cell cultures. In some embodiments, amino acids provided in or used to supplement cell culture medium may be provided as salts or in hydrate form.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Batch culture: The term "batch culture" as used herein refers to a method of culturing cells in which all the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified.

Bioavailability: As used herein, the term "bioavailability" generally refers to the percentage of the administered dose that reaches the blood stream of a subject.

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. Biological activity can also be determined by in vitro assays (for example, in vitro enzymatic assays such as sulfate release assays). In particular embodiments, where a protein or polypeptide is biologically active, a portion of that protein or polypeptide that shares at least one biological activity of the protein or polypeptide is typically referred to as a "biologically active" portion. In some embodiments, a protein is produced and/or purified from a cell culture system, which displays biologically activity when administered to a subject. In some embodiments, a protein requires further processing in order to become biologically active. In some embodiments, a protein requires posttranslational modification such as, but is not limited to, glycosylation (e.g., sialylation), farnesylation, cleavage, folding, formylglycine conversion and combinations thereof, in order to become biologically active. In some embodiments, a protein produced as a proform (i.e. immature form), may require additional modification to become biologically active.

Bioreactor: The term "bioreactor" as used herein refers to a vessel used for the growth of a host cell culture. A bioreactor can be of any size so long as it is useful for the culturing of mammalian cells. Typically, a bioreactor will be at least 1 liter and may be 10, 100, 250, 500, 1000, 2500, 5000, 8000, 10,000, 12,0000 liters or more, or any volume in between. Internal conditions of a bioreactor, including, but not limited to pH, osmolarity, $CO_2$ saturation, $O_2$ saturation, temperature and combinations thereof, are typically controlled during the culturing period. A bioreactor can be composed of any material that suitable for holding cells in media under the culture conditions of the present invention, including glass, plastic or metal. In some embodiments, a bioreactor may be used for performing animal cell culture. In some embodiments, a bioreactor may be used for performing mammalian cell culture. In some embodiments, a bioreactor may be used with cells and/or cell lines derived from such organisms as, but not limited to, mammalian cell, insect cells, bacterial cells, yeast cells and human cells. In some embodiments, a bioreactor is used for large-scale cell culture production and is typically at least 100 liters and may be 200, 500, 1000, 2500, 5000, 8000, 10,000, 12,0000 liters or more, or any volume in between. One of ordinary skill in the art will be aware of and will be able to choose suitable bioreactors for use in practicing the present invention.

Cell culture: These terms as used herein refer to a cell population that is gown in a medium under conditions suitable to survival and/or growth of the cell population. As will be clear to those of ordinary skill in the art, these terms as used herein may refer to the combination comprising the cell population and the medium in which the population is grown.

Cultivation: As used herein, the term "cultivation" or grammatical equivalents refers to a process of maintaining cells under conditions favoring growth or survival. The terms "cultivation" and "cell culture" or any synonyms are used interchangeably in this application.

Culture vessel: As used herein, the term "culture vessel" refers to any container that can provide an aseptic environment for culturing cells. Exemplary culture vessels include, but are not limited to, glass, plastic, or metal containers.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodstream. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Fed-batch culture: The term "fed-batch culture" as used herein refers to a method of culturing cells in which additional components are provided to the culture at some time subsequent to the beginning of the culture process. The provided components typically comprise nutritional supplements for the cells which have been depleted during the culturing process. A fed-batch culture is typically stopped at some point and the cells and/or components in the medium are harvested and optionally purified.

Fragment: The term "fragment" as used herein refers to polypeptides and is defined as any discrete portion of a given polypeptide that is unique to or characteristic of that polypeptide. The term as used herein also refers to any discrete portion of a given polypeptide that retains at least a fraction of the activity of the full-length polypeptide. Preferably the fraction of activity retained is at least 10% of the activity of the full-length polypeptide. More preferably the fraction of activity retained is at least 20%, 30%, 40%, 50%, 60%, 70%, 80% or 90% of the activity of the full-length polypeptide. More preferably still the fraction of activity retained is at least 95%, 96%, 97%, 98% or 99% of the activity of the full-length polypeptide. Most preferably, the fraction of activity retained is 100% of the activity of the full-length polypeptide. The term as used herein also refers to any portion of a given polypeptide that includes at least an established sequence element found in the full-length polypeptide. Preferably, the sequence element spans at least 4-5, more preferably at least about 10, 15, 20, 25, 30, 35, 40, 45, 50 or more amino acids of the full-length polypeptide.

Gene: The term "gene" as used herein refers to any nucleotide sequence, DNA or RNA, at least some portion of which encodes a discrete final product, typically, but not limited to, a polypeptide, which functions in some aspect of a cellular process. The term is not meant to refer only to the coding sequence that encodes the polypeptide or other discrete final product, but may also encompass regions preceding and following the coding sequence that modulate the basal level of expression, as well as intervening sequences ("introns") between individual coding segments ("exons"). In some embodiments, a gene may include regulatory sequences (e.g., promoters, enhancers, poly adenylation sequences, termination sequences, kozac sequences, tata box, etc.) and/or modification sequences. In some embodiments, a gene may include references to nucleic acids that do not encode proteins but rather encode functional RNA molecules such as tRNAs, RNAi-inducing agents, etc.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Genetic control element: The term "genetic control element" as used herein refers to any sequence element that modulates the expression of a gene to which it is operably linked. Genetic control elements may function by either increasing or decreasing the expression levels and may be located before, within or after the coding sequence. Genetic control elements may act at any stage of gene expression by regulating, for example, initiation, elongation or termination of transcription, mRNA splicing, mRNA editing, mRNA stability, mRNA localization within the cell, initiation, elongation or termination of translation, or any other stage of gene expression. Genetic control elements may function individually or in combination with one another.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM 120 weight residue table, a gap length penalty of 12 and a gap penalty of 4. The percent identity between two nucleotide sequences can, alternatively, be determined using the GAP program in the GCG software package using an NWSgapdna.CMP matrix. Various other sequence alignment programs are available and can be used to determine sequence identity such as, for example, Clustal.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.)

Medium: The terms as used herein refer to a solution containing nutrients which nourish growing cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. In some embodiments, medium is formulated to a pH and salt concentration optimal for cell survival and proliferation. In some embodiments, medium may be a "chemically defined medium"—a serum-free media that contains no proteins, hydrolysates or components of unknown composition. In some embodiment, chemically defined medium is free of animal-derived components and all components within the medium have a known chemical structure. In some embodiments, medium may be a "serum based medium"—a medium that has been supplemented animal derived components such as, but not limited to, fetal calf serum, horse serum, goat serum, donkey serum and/or combinations thereof.

Nucleic acid: As used herein, the term "nucleic acid," in its broadest sense, refers to a compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Perfusion process: The term "perfusion process" as used herein refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium are typically harvested on a continuous or semi-continuous basis and are optionally purified. Typically, a cell culture process involving a perfusion process is referred to as "perfusion culture." Typically, nutritional supplements are provided in a fresh medium during a perfusion process. In some embodiments, a fresh medium may be identical or similar to the base medium used in the cell culture process. In some embodiments, a fresh medium may be different than the base medium but containing desired nutritional supplements. In some embodiments, a fresh medium is a chemically-defined medium.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. In some embodiments, a protein can sometimes include more than one polypeptide chain, for example linked by one or more disulfide bonds or associated by other means. In some embodiments, polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Recombinant protein and Recombinant polypeptide: These terms as used herein refer to a polypeptide expressed from a host cell, that has been genetically engineered to express that polypeptide. In some embodiments, a recombinant protein may be expressed in a host cell derived from an animal. In some embodiments, a recombinant protein may be expressed in a host cell derived from an insect. In some embodiments, a recombinant protein may be expressed in a host cell derived from a yeast. In some embodiments, a recombinant protein may be expressed in a host cell derived from a prokaryote. In some embodiments, a recombinant protein may be expressed in a host cell derived from an mammal. In some embodiments, a recombinant protein may be expressed in a host cell derived from a human. In some embodiments, the recombinantly expressed polypeptide may be identical or similar to a polypeptide that is normally expressed in the host cell. In some embodiments, the recombinantly expressed polypeptide may be foreign to the host cell, i.e. heterologous to peptides normally expressed in the host cell. Alternatively, in some embodiments the recombinantly expressed polypeptide can be a chimeric, in that portions of the polypeptide contain amino acid sequences that are identical or similar to polypeptides normally expressed in the host cell, while other portions are foreign to the host cell.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Vector: As used herein, "vector" refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DETAILED DESCRIPTION OF THE INVENTION

The present invention provides, among other things, methods and compositions for production of recombinant I2S protein with improved potency and activity using cells co-expressing I2S and FGE protein. In some embodiments, cells according to the present invention are engineered to simultaneously over-express recombinant I2S and FGE proteins. Cells according to the invention are adaptable to various cell culture conditions. In some embodiments, cells of the present invention are adaptable to a large-scale suspension serum-free culture.

Various aspects of the invention are described in further detail in the following subsections. The use of subsections is not meant to limit the invention. Each subsection may apply to any aspect of the invention. In this application, the use of "or" means "and/or" unless stated otherwise.

Iduronate-2-sulfatase (I2S)

As used herein, an I2S protein is any protein or a portion of a protein that can substitute for at least partial activity of naturally-occurring Iduronate-2-sulfatase (I2S) protein or rescue one or more phenotypes or symptoms associated with I2S-deficiency. As used herein, the terms "an I2S enzyme" and "an I2S protein", and grammatical equivalents, are used interchangeably.

Typically, the human I2S protein is produced as a precursor form. The precursor form of human I2S contains a signal peptide (amino acid residues 1-25 of the full length precursor), a pro-peptide (amino acid residues 26-33 of the full length precursor), and a chain (residues 34-550 of the full length precursor) that may be further processed into the 42 kDa chain (residues 34-455 of the full length precursor) and the 14 kDa chain (residues 446-550 of the full length precursor). Typically, the precursor form is also referred to as full-length precursor or full-length I2S protein, which contains 550 amino acids. The amino acid sequences of the mature form (SEQ ID NO:1) having the signal peptide removed and full-length precursor (SEQ ID NO:2) of a typical wild-type or naturally-occurring human I2S protein are shown in Table 1. The signal peptide is underlined. In addition, the amino acid sequences of human I2S protein isoform a and b precursor are also provided in Table 1, SEQ ID NO:3 and 4, respectively.

TABLE 1

| | Human Iduronate-2-sulfatase |
|---|---|
| Mature Form | SETQANSTTDALNVLLIIVDDLRPSLGCYGDKLVRSPNIDQLASHSLLFQNAFA<br>QQAVCAPSRVSFLTGRRPDTTRLYDFNSYWRVHAGNFSTIPQYFKENGYVTMSV<br>GKVFHPGISSNHTDDSPYSWSFPPYHPSSEKYENTKTCRGPDGELHANLLCPVD<br>VLDVPEGTLPDKQSTEQATQLLEKMKTSASPFFLAVGYHKPHIPFRYPKEFQKL<br>YPLENITLAPDPEVPDGLPPVAYNPWMDIRQREDVQALNISVPYGPIPVDFQRK<br>IRQSYFASVSYLDTQVGRLLSALDDLQLANSTITAFTSDHGWALGEHGEWAKYS<br>NFDVATHVPLIFYVPGRTASLPEAGEKLFPYLDPFDSASQLMEPGRQSMDLVEL<br>VSLFPTLAGLAGLQVPPRCPVPSFHVELCREGKNLLKHFRFRDLEEDPYLPGNP<br>RELIAYSQYPRPSDIPQWNSDKPSLKDIKIMGYSIRTIDYRYTVWVGFNPDEFL<br>ANFSDIHAGELYFVDSDPLQDHNMYNDSQGGDLFQLLMP (SEQ ID NO: 1) |
| Full-Length<br>Precursor<br>(Isoform a) | <u>MPPPRTGRGLLWLGLVLSSVCVALG</u>SETQANSTTDALNVLLIIVDDLRPSLGCY<br>GDKLVRSPNIDQLASHSLLFQNAFAQQAVCAPSRVSFLTGRRPDTTRLYDFNSY<br>WRVHAGNFSTIPQYFKENGYVTMSVGKVFHPGISSNHTDDSPYSWSFPPYHPSS<br>EKYENTKTCRGPDGELHANLLCPVDVLDVPEGTLPDKQSTEQAIQLLEKMKTSA<br>SPFFLAVGYHKPHIPFRYPKEFQKLYPLENITLAPDPEVPDGLPPVAYNPWMDI<br>RQREDVQALNISVPYGPIPVDFQRKIRQSYFASVSYLDTQVGRLLSALDDLQLA<br>NSTIIAFTSDHGWALGEHGEWAKYSNFDVATHVPLIFYVPGRTASLPEAGEKLF<br>PYLDPFDSASQLMEPGRQSMDLVELVSLFPTLAGLAGLQVPPRCPVPSFHVELC<br>REGKNLLKHFRFRDLEEDPYLPGNPRELIAYSQYPRPSDIPQWNSDKPSLKDIK<br>IMGYSIRTIDYRYTVWVGFNPDEFLANFSDIHAGELYFVDSDPLQDHNMYNDSQ<br>GGDLFQLLMP(SEQ ID NO: 2) |
| Isoform b Precursor | MPPPRTGRGLLWLGLVLSSVCVALGSETQANSTTDALNVLLIIVDDLRPSLGCY<br>GDKLVRSPNIDQLASHSLLFQNAFAQQAVCAPSRVSFLTGRRPDTTRLYDFNSY<br>WRVHAGNFSTIPQYFKENGYVTMSVGKVFHPGISSNHTDDSPYSWSFPPYHPSS |

TABLE 1-continued

Human Iduronate-2-sulfatase

| | |
|---|---|
| | EKYENTKTCRGPDGELHANLLCPVDVLDVPEGTLPDKQSTEQAIQLLEKMKTSA<br>SPFFLAVGYHKPHIPFRYPKEFQKLYPLENITLAPDPEVPDGLPPVAYNPWMDI<br>RQREDVQALNISVPYGPIPVDFQEDQSSTGFRLKTSSTRKYK<br>(SEQ ID NO: 3) |
| Isoform c Precursor | MPPPRTGRGLLWLGLVLSSVCVALGSETQANSTTDALNVLLIIVDDLRPSLGCY<br>GDKLVRSPNIDQLASHSLLFQNAFAQQAVCAPSRVSFLTGRRPDTTRLYDFNSY<br>WRVHAGNFSTIPQYFKENGYVTMSVGKVFHPGISSNHTDDSPYSWSFPPYHPSS<br>EKYENTKTCRGPDGELHANLLCPVDVLDVPEGTLPDKQSTEQAIQLLEKMKTSA<br>SPFFLAVGYHKPHIPFRYPKEFQKLYPLENITLAPDPEVPDGLPPVAYNPWMDI<br>RQREDVQALNISVPYGPIPVDFQRKIRQSYFASVSYLDTQVGRLLSALDDLQLA<br>NSTIIAFTSDHGFLMRTNT(SEQ ID No: 4) |

Thus, in some embodiments, an I2S enzyme is mature human I2S protein (SEQ ID NO:1). As disclosed herein, SEQ ID NO:1 represents the canonical amino acid sequence for the human I2S protein. In some embodiments, the I2S protein may be a splice isoform and/or variant of SEQ ID NO:1, resulting from transcription at an alternative start site within the 5' UTR of the I2S gene. In some embodiments, a suitable replacement enzyme may be a homologue or an analogue of mature human I2S protein. For example, a homologue or an analogue of mature human I2S protein may be a modified mature human I2S protein containing one or more amino acid substitutions, deletions, and/or insertions as compared to a wild-type or naturally-occurring I2S protein (e.g., SEQ ID NO:1), while retaining substantial I2S protein activity. Thus, in some embodiments, a replacement enzyme suitable for the present invention is substantially homologous to mature human I2S protein (SEQ ID NO:1). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a replacement enzyme suitable for the present invention is substantially identical to mature human I2S protein (SEQ ID NO:1). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a replacement enzyme suitable for the present invention contains a fragment or a portion of mature human I2S protein.

Alternatively, an I2S enzyme is full-length I2S protein. In some embodiments, an I2S enzyme may be a homologue or an analogue of full-length human I2S protein. For example, a homologue or an analogue of full-length human I2S protein may be a modified full-length human I2S protein containing one or more amino acid substitutions, deletions, and/or insertions as compared to a wild-type or naturally-occurring full-length I2S protein (e.g., SEQ ID NO:2), while retaining substantial I2S protein activity. Thus, In some embodiments, an I2S enzyme is substantially homologous to full-length human I2S protein (SEQ ID NO:2). In some embodiments, an I2S enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, an I2S enzyme suitable for the present invention is substantially identical to SEQ ID NO:2. In some embodiments, an I2S enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, an I2S enzyme suitable for the present invention contains a fragment or a portion of full-length human I2S protein. As used herein, a full-length I2S protein typically contains signal peptide sequence.

In some embodiments, an I2S enzyme suitable for the present invention is human I2S isoform a protein. In some embodiments, a suitable I2S enzyme may be a homologue or an analogue of human I2S isoform a protein. For example, a homologue or an analogue of human I2S isoform a protein may be a modified human I2S isoform a protein containing one or more amino acid substitutions, deletions, and/or insertions as compared to a wild-type or naturally-occurring human I2S isoform a protein (e.g., SEQ ID NO:3), while retaining substantial I2S protein activity. Thus, in some embodiments, an I2S enzyme is substantially homologous to human I2S isoform a protein (SEQ ID NO:3). In some embodiments, an I2S enzyme has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:3. In some embodiments, an I2S enzyme is substantially identical to SEQ ID NO:3. In some embodiments, an I2S enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:3. In some embodiments, an I2S enzyme suitable for the present invention contains a fragment or a portion of human I2S isoform a protein. As used herein, a human I2S isoform a protein typically contains a signal peptide sequence.

In some embodiments, an I2S enzyme is human I2S isoform b protein. In some embodiments, an I2S enzyme may be a homologue or an analogue of human I2S isoform b protein. For example, a homologue or an analogue of human I2S isoform b protein may be a modified human I2S isoform b protein containing one or more amino acid substitutions, deletions, and/or insertions as compared to a wild-type or naturally-occurring human I2S isoform b protein (e.g., SEQ ID NO:4), while retaining substantial I2S protein activity. Thus, In some embodiments, an I2S enzyme is substantially homologous to human I2S isoform b protein (SEQ ID NO:4). In some embodiments, an I2S enzyme has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:4. In some embodiments, an I2S enzyme is substantially identical to SEQ ID NO:4. In some embodiments, an I2S enzyme has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:4. In some embodiments, an I2S enzyme suitable for the present invention contains a fragment or a portion of human I2S isoform b protein. As used herein, a human I2S isoform b protein typically contains a signal peptide sequence.

Homologues or analogues of human I2S proteins can be prepared according to methods for altering polypeptide sequence known to one of ordinary skill in the art such as are found in references that compile such methods. In some embodiments, conservative substitutions of amino acids include substitutions made among amino acids within the following groups: (a) M, I, L, V; (b) F, Y, W; (c) K, R, H; (d) A, G; (e) S, T; (f) Q, N; and (g) E, D. In some embodiments, a "conservative amino acid substitution" refers to an amino acid substitution that does not alter the relative charge or size characteristics of the protein in which the amino acid substitution is made.

In some embodiments, I2S enzymes contain a moiety that binds to a receptor on the surface of cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. A suitable lysosomal targeting moiety can be IGF-I, IGF-II, RAP, p97, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence). In some embodiments, a suitable receptor that the M6P residues bind may be cation-dependent.

Formylglycine Generating Enzyme (FGE)

Typically, the enzyme activity of I2S is influenced by a post-translational modification of a conserved cysteine (e.g., corresponding to amino acid 59 of the mature human I2S (SEQ ID NO:1)) to formylglycine, which is also referred to as 2-amino-3-oxopropionic acid, or oxo-alanine. This post-translational modification generally occurs in the endoplasmic reticulum during protein synthesis and is catalyzed by Formylglycine Generating Enzyme (FGE). The specific enzyme activity of I2S is typically positively correlated with the extent to which the I2S has the formylglycine modification. For example, an I2S protein preparation that has a relatively high amount of formylglycine modification typically has a relatively high specific enzyme activity; whereas an I2S protein preparation that has a relatively low amount of formylglycine modification typically has a relatively low specific enzyme activity.

Thus, cells suitable for producing recombinant I2S protein according to the present invention typically also express FGE protein. In some embodiments, suitable cells express an endogenous FGE protein. In some embodiments, suitable cells are engineered to express an exogenous (also referred to as recombinant) Formylglycine Generating Enzyme (FGE) in combination with recombinant I2S. In some embodiments, suitable cells are engineered to activate an endogenous FGE gene such that the expression level or activity of the FGE protein is increased.

Typically, the human FGE protein is produced as a precursor form. The precursor form of human FGE contains a signal peptide (amino acid residues 1-33 of the full length precursor) and a chain (residues 34-374 of the full length precursor). Typically, the precursor form is also referred to as full-length precursor or full-length FGE protein, which contains 374 amino acids. The amino acid sequences of the mature form (SEQ ID NO:5) having the signal peptide removed and full-length precursor (SEQ ID NO:6) of a typical wild-type or naturally-occurring human FGE protein are shown in Table 2.

TABLE 2

| | Human Formylglycine Generating Enzyme (FGE) |
|---|---|
| Mature Form | SQEAGTGAGAGSLAGSCGCGTPQRPGAHGSSAAAHRYSREANAPGPVPGERQLA HSKMVPIPAGVFTMGTDDPQIKQDGEAPARRVTIDAFYMDAYEVSNTEFEKFVN STGYLTEAEKFGDSFVFEGMLSEQVKTNIQQAVAAAPWWLPVKGANWRHPEGPD STILHRPDHPVLHVSWNDAVAYCTWAGKRLPTEAEWEYSCRGGLHNRLFPWGNK LQPKGQHYANIWQGEFPVTNTGEDGFQGTAPVDAFPPNGYGLYNIVGNAWEWTS DWWTVHHSVEETLNPKGPPSGKDRVKKGGSYMCHRSYCYRYRCAARSQNTPDSS ASNLGFRCAADRLPTMD (SEQ ID NO: 5) |
| Full-Length Precursor | MAAPALGLVCGRCPELGLVLLLLLLSLLCGAAGSQEAGTGAGAGSLAGSCGCGT PQRPGAHGSSAAAHRYSREANAPGPVPGERQLAHSKMVPIPAGVFTMGTDDPQI KQDGEAPARRVTIDAFYMDAYEVSNTEFEKFVNSTGYLTEAEKFGDSFVFEGML SEQVKTNIQQAVAAAPWWLPVKGANWRHPEGPDSTILHRPDHPVLHVSWNDAVA YCTWAGKRLPTEAEWEYSCRGGLHNRLFPWGNKLQPKGQHYANIWQGEFPVTNT GEDGFQGTAPVDAFPPNGYGLYNIVGNAWEWTSDWWTVHHSVEETLNPKGPPSG KDRVKKGGSYMCHRSYCYRYRCAARSQNTPDSSASNLGFRCAADRLPTMD (SEQ ID NO: 6) |

Thus, in some embodiments, an FGE enzyme suitable for the present invention is mature human FGE protein (SEQ ID NO:5). In some embodiments, a suitable FGE enzyme may be a homologue or an analogue of mature human FGE protein. For example, a homologue or an analogue of mature human FGE protein may be a modified mature human FGE protein containing one or more amino acid substitutions, deletions, and/or insertions as compared to a wild-type or naturally-occurring FGE protein (e.g., SEQ ID NO:5), while retaining substantial FGE protein activity. Thus, in some embodiments, an FGE enzyme suitable for the present invention is substantially homologous to mature human FGE protein (SEQ ID NO:5). In some embodiments, an FGE enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:5. In some embodiments, an FGE enzyme suitable for the present invention is substantially identical to mature human FGE protein (SEQ ID NO:5). In some embodiments, an FGE enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:5. In some embodiments, an FGE enzyme suitable for the present invention contains a fragment or a portion of mature human FGE protein.

Alternatively, an FGE enzyme suitable for the present invention is full-length FGE protein. In some embodiments, an FGE enzyme may be a homologue or an analogue of full-length human FGE protein. For example, a homologue or an analogue of full-length human FGE protein may be a modified full-length human FGE protein containing one or more amino acid substitutions, deletions, and/or insertions as compared to a wild-type or naturally-occurring full-length FGE protein (e.g., SEQ ID NO:6), while retaining substantial FGE protein activity. Thus, in some embodiments, an FGE enzyme suitable for the present invention is substantially homologous to full-length human FGE protein (SEQ ID NO:6). In some embodiments, an FGE enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:4. In some embodiments, an FGE enzyme suitable for the present invention is substantially identical to SEQ ID NO:6. In some embodiments, an FGE enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:6. In some embodiments, an FGE enzyme suitable for the present invention contains a fragment or a portion of full-length human FGE protein. As used herein, a full-length FGE protein typically contains signal peptide sequence.

Exemplary nucleic acid sequences and amino acid sequences encoding exemplary FGE proteins are disclosed US Publication No. 20040229250, the entire contents of which is incorporated herein by reference.

Cells Co-Expressing I2S and FGE

The present invention recognizes the need for the high-level, commercial production of biologically active I2S using a cell culture system. Because a large number of production factors can influence the selection of a specific host cell, nucleic acid molecules disclosed in the present specification are directed toward a wide range of prokaryotic and eukaryotic cells and/or cell lines including, without limitation, cell lines derived from bacteria strains, yeast strains, insect cells, animal cells, mammalian cells and human cells. Aspects of the present invention also provide for expression constructs and the generation of recombinant stable cell lines useful for expressing naturally occurring, as well as, modified I2S and/or FGE proteins which are disclosed in the present specification. In addition, aspects of the present invention also provide methods for producing cell lines that express I2S and FGE using the disclosed nucleic acid sequences of the present specification.

Nucleic Acids Encoding I2S and/or FGE Proteins

In some embodiments, nucleic acid molecules are provided comprising nucleic acid sequences encoding for a recombinant gene of interest (herein referred to as a transgene) such as an I2S and/or FGE protein described in various embodiments herein. In some embodiments, the nucleic acid encoding a transgene may be modified to provide increased expression of the encoded I2S and/or FGE protein, which is also referred to as codon optimization. For example, the nucleic acid encoding a transgene can be modified by altering the open reading frame for the coding sequence. As used herein, the term "open reading frame" is synonymous with "ORF" and means any nucleotide sequence that is potentially able to encode a protein, or a portion of a protein. An open reading frame usually begins with a start codon (represented as, e.g. AUG for an RNA molecule and ATG in a DNA molecule in the standard code) and is read in codon-triplets until the frame ends with a STOP codon (represented as, e.g. UAA, UGA or UAG for an RNA molecule and TAA, TGA or TAG in a DNA molecule in the standard code). As used herein, the term "codon" means a sequence of three nucleotides in a nucleic acid molecule that specifies a particular amino acid during protein synthesis; also called a triplet or codon-triplet. For example, of the 64 possible codons in the standard genetic code, two codons, GAA and GAG encode the amino acid Glutamine whereas the codons AAA and AAG specify the amino acid Lysine. In the standard genetic code three codons are stop codons, which do not specify an amino acid. As used herein, the term "synonymous codon" means any and all of the codons that code for a single amino acid. Except for Methionine and Tryptophan, amino acids are coded by two to six synonymous codons. For example, in the standard genetic code the four synonymous codons that code for the amino acid Alanine are GCA, GCC, GCG and GCU, the two synonymous codons that specify Glutamine are GAA and GAG and the two synonymous codons that encode Lysine are AAA and AAG.

In some embodiments, a nucleic acid encoding the open reading frame of an I2S and/or FGE protein may be modified using standard codon optimization methods. Various commercial algorithms for codon optimization are available and can be used to practice the present invention. Typically, codon optimization does not alter the encoded amino acid sequences. In some embodiments, codon optimization may lead to amino acids alteration such as substitution, deletion or insertion. Typically, such amino acid alteration does not substantially alter the protein activity.

Exemplary nucleic acid sequences encoding an I2S and FGE proteins, respectively are shown in SEQ ID NO:7 and 8 below.

```
                                                          SEQ ID NO: 7
Exemplary nucleic acid sequence encoding iduronate 2-sulfatase (I2S)
ATGCCCCCGCCCCGCACCGGCCGCGGCCTGCTGTGGCTGGGCCTGGTGCTGAGCAGCGTGTGCGTGGC

CCTGGGCAGCGAGACCCAGGCCAACAGCACCACCGACGCCCTGAACGTGCTGCTGATCATCGTGGAC

GACCTGCGCCCCAGCCTGGGCTGCTACGGCGACAAGCTGGTGCGCAGCCCCAACATCGACCAGCTGGC

CAGCCACAGCCTGCTGTTCCAGAACGCCTTCGCCCAGCAGGCCGTGTGCGCCCCCAGCCGCGTGAGCT

TCCTGACCGGCCGCCGCCCCGACACCACCCGCCTGTACGACTTCAACAGCTACTGGCGCGTGCACGCC

GGCAACTTCAGCACCATCCCCCAGTACTTCAAGGAGAACGGCTACGTGACCATGAGCGTGGGCAAGGT

GTTCCACCCCGGCATCAGCAGCAACCACACCGACGACAGCCCCTACAGCTGGAGCTTCCCCCCCTACC

ACCCCAGCAGCGAGAAGTACGAGAACACCAAGACCTGCCGCGGCCCCGACGGCGAGCTGCACGCCAA

CCTGCTGTGCCCCGTGGACGTGCTGGACGTGCCCGAGGGCACCCTGCCCGACAAGCAGAGCACCGAGC
```

-continued
```
AGGCCATCCAGCTGCTGGAGAAGATGAAGACCAGCGCCAGCCCCTTCTTCCTGGCCGTGGGCTACCAC

AAGCCCCACATCCCCTTCCGCTACCCCAAGGAGTTCCAGAAGCTGTACCCCCTGGAGAACATCACCCT

GGCCCCCGACCCCGAGGTGCCCGACGGCCTGCCCCCCGTGGCCTACAACCCCTGGATGGACATCCGCC

AGCGCGAGGACGTGCAGGCCCTGAACATCAGCGTGCCCTACGGCCCCATCCCCGTGGACTTCCAGCGC

AAGATCCGCCAGAGCTACTTCGCCAGCGTGAGCTACCTGGACACCCAGGTGGGCCGCCTGCTGAGCGC

CCTGGACGACCTGCAGCTGGCCAACAGCACCATCATCGCCTTCACCAGCGACCACGGCTGGGCCCTGG

GCGAGCACGGCGAGTGGGCCAAGTACAGCAACTTCGACGTGGCCACCCACGTGCCCCTGATCTTCTAC

GTGCCCGGCCGCACCGCCAGCCTGCCCGAGGCCGGCGAGAAGCTGTTCCCCTACCTGGACCCCTTCGA

CAGCGCCAGCCAGCTGATGGAGCCCGGCCGCCAGAGCATGGACCTGGTGGAGCTGGTGAGCCTGTTCC

CCACCCTGGCCGGCCTGGCCGGCCTGCAGGTGCCCCCCCGCTGCCCCGTGCCCAGCTTCCACGTGGAG

CTGTGCCGCGAGGGCAAGAACCTGCTGAAGCACTTCCGCTTCCGCGACCTGGAGGAGGACCCCTACCT

GCCCGGCAACCCCCGCGAGCTGATCGCCTACAGCCAGTACCCCCGCCCAGCGACATCCCCCAGTGGA

ACAGCGACAAGCCCAGCCTGAAGGACATCAAGATCATGGGCTACAGCATCCGCACCATCGACTACCG

CTACACCGTGTGGGTGGGCTTCAACCCCGACGAGTTCCTGGCCAACTTCAGCGACATCCACGCCGGCG

AGCTGTACTTCGTGGACAGCGACCCCCTGCAGGACCACAACATGTACAACGACAGCCAGGGCGGCGA

CCTGTTCCAGCTGCTGATGCCCTAG
```

SEQ ID NO: 8
Exemplary nucleic acid sequence encoding full-length precursor formylglycine generating enzyme (FGE)
```
ATGGCTGCGCCCGCACTAGGGCTGGTGTGTGGACGTTGCCCTGAGCTGGGTCTCGTCCTCTTGCTGCTG

CTGCTCTCGCTGCTGTGTGGAGCGGCAGGGAGCCAGGAGGCCGGGACCGGTGCGGGCGCGGGGTCCC

TTGCGGGTTCTTGCGGCTGCGGCACGCCCCAGCGGCCTGGCGCCCATGGCAGTTCGGCAGCCGCTCAC

CGATACTCGCGGGAGGCTAACGCTCCGGGCCCCGTACCCGGAGAGCGGCAACTCGCGCACTCAAAGA

TGGTCCCCATCCCTGCTGGAGTATTTACAATGGGCACAGATGATCCTCAGATAAAGCAGGATGGGGAA

GCACCTGCGAGGAGAGTTACTATTGATGCCTTTTACATGGATGCCTATGAAGTCAGTAATACTGAATTT

GAGAAGTTTGTGAACTCAACTGGCTATTTGACAGAGGCTGAGAAGTTTGGCGACTCCTTTGTCTTTGAA

GGCATGTTGAGTGAGCAAGTGAAGACCAATATTCAACAGGCAGTTGCAGCTGCTCCCTGGTGGTTACC

TGTGAAAGGCGCTAACTGGAGACACCCAGAAGGGCCTGACTCTACTATTCTGCACAGGCCGGATCATC

CAGTTCTCCATGTGTCCTGGAATGATGCGTTGCCTACTGCACTTGGGCAGGGAAGCGGCTGCCCACG

GAAGCTGAGTGGGAATACAGCTGTCGAGGAGGCCTGCATAATAGACTTTTCCCTGGGGCAACAAACT

GCAGCCCAAAGGCCAGCATTATGCCAACATTTGGCAGGGCGAGTTTCCGGTGACCAACACTGGTGAGG

ATGGCTTCCAAGGAACTGCGCCTGTTGATGCCTTCCCTCCCAATGGTTATGGCTTATACAACATAGTGG

GGAACGCATGGGAATGGACTTCAGACTGGTGGACTGTTCATCATTCTGTTGAAGAAACGCTTAACCCA

AAAGGTCCCCCTTCTGGGAAAGACCGAGTGAAGAAAGGTGGATCCTACATGTGCCATAGGTCTTATTG

TTACAGGTATCGCTGTGCTGCTCGGAGCCAGAACACACCTGATAGCTCTGCTTCGAATCTGGGATTCCG

CTGTGCAGCCGACCGCCTGCCCACCATGGACTGA
```

In some embodiments, a nucleotide change may alter a synonymous codon within the open reading frame in order to agree with the endogenous codon usage found in a particular heterologous cell selected to express I2S and/or FGE. Alternatively or additionally, a nucleotide change may alter the G+C content within the open reading frame to better match the average G+C content of open reading frames found in endogenous nucleic acid sequence present in the heterologous host cell. A nucleotide change may also alter a polymononucleotide region or an internal regulatory or structural site found within an I2S or FGE sequence. Thus, a variety of modified or optimized nucleotide sequences are envisioned including, without limitation, nucleic acid sequences providing increased expression of I2S and/or FGE proteins in a prokaryotic cell; yeast cell; insect cell; and in a mammalian cell.

Thus, in some embodiments, a nucleic acid encoding an I2S protein suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:7. In some embodiments, a nucleic acid encoding an FGE protein suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:8. Typically, a modified nucleic acid encodes an I2S and/or FGE protein with or without amino acid sequence alteration. In the event there is amino acid alteration, such alteration typically does not substantially alter the I2S or FGE protein activity.

Expression Vectors

A nucleic acid sequence encoding an I2S and/or FGE protein as described in the present application, can be molecularly cloned (inserted) into a suitable vector for propagation or expression in a host cell. A wide variety of expression vectors can be used to practice the present invention, including, without limitation, a prokaryotic expression vector; a yeast expression vector; an insect expression vector and a mammalian expression vector. Exemplary vectors suitable for the present invention include, but are not limited to, viral based vectors (e.g., AAV based vectors, retrovirus based vectors, plasmid based vectors). In some embodiments, nucleic acid sequences encoding an I2S and FGE proteins, respectively can be inserted in separate vectors. In some embodiments, nucleic acid sequences encoding an I2S and FGE proteins, respectively can be inserted in a same vector. Typically, a nucleic acid encoding an I2S or FGE protein is operably linked to various regulatory sequences or elements.

Regulatory Sequences or Elements

Various regulatory sequences or elements may be incorporated in an expression vector suitable for the present invention. Exemplary regulatory sequences or elements include, but are not limited to, promoters, enhancers, repressors or suppressors, 5' untranslated (or non-coding) sequences, introns, 3' untranslated (or non-coding) sequences.

As used herein, a "Promoter" or "Promoter sequence" is a DNA regulatory region capable of binding an RNA polymerase in a cell (e.g., directly or through other promoter bound proteins or substances) and initiating transcription of a coding sequence. A promoter sequence is, in general, bound at its 3' terminus by the transcription initiation site and extends upstream (5' direction) to include the minimum number of bases or elements necessary to initiate transcription at any level. The promoter may be operably associated with or operably linked to the expression control sequences, including enhancer and repressor sequences or with a nucleic acid to be expressed. In some embodiments, the promoter may be inducible. In some embodiments, the inducible promoter may be unidirectional or bio-directional. In some embodiments, the promoter may be a constitutive promoter. In some embodiments, the promoter can be a hybrid promoter, in which the sequence containing the transcriptional regulatory region is obtained from one source and the sequence containing the transcription initiation region is obtained from a second source. Systems for linking control elements to coding sequence within a transgene are well known in the art (general molecular biological and recombinant DNA techniques are described in Sambrook, Fritsch, and Maniatis, *Molecular Cloning: A Laboratory Manual*, Second Edition, Cold Spring Harbor Laboratory Press, Cold Spring Harbor, N.Y., 1989, which is incorporated herein by reference). Commercial vectors suitable for inserting a transgene for expression in various host cells under a variety of growth and induction conditions are also well known in the art.

In some embodiments, a specific promoter may be used to control expression of the transgene in a mammalian host cell such as, but are not limited to, SRα-promoter (Takebe et al., Molec. and Cell. Bio. 8:466-472 (1988)), the human CMV immediate early promoter (Boshart et al., Cell 41:521-530 (1985); Foecking et al., Gene 45:101-105 (1986)), human CMV promoter, the human CMV5 promoter, the murine CMV immediate early promoter, the EF1-α-promoter, a hybrid CMV promoter for liver specific expression (e.g., made by conjugating CMV immediate early promoter with the transcriptional promoter elements of either human α-1-antitrypsin (HAT) or albumin (HAL) promoter), or promoters for hepatoma specific expression (e.g., wherein the transcriptional promoter elements of either human albumin (HAL; about 1000 bp) or human α-1-antitrypsin (HAT, about 2000 bp) are combined with a 145 long enhancer element of human α-1-microglobulin and bikunin precursor gene (AMBP); HAL-AMBP and HAT-AMBP); the SV40 early promoter region (Benoist at al., Nature 290:304-310 (1981)), the Orgyia pseudotsugata immediate early promoter, the herpes thymidine kinase promoter (Wagner at al., Proc. Natl. Acad. Sci. USA 78:1441-1445 (1981)); or the regulatory sequences of the metallothionein gene (Brinster et al., Nature 296:39-42 (1982)). In some embodiments, the mammalian promoter is a is a constitutive promoter such as, but not limited to, the hypoxanthine phosphoribosyl transferase (HPTR) promoter, the adenosine deaminase promoter, the pyruvate kinase promoter, the beta-actin promoter as well as other constitutive promoters known to those of ordinary skill in the art.

In some embodiments, a specific promoter may be used to control expression of a transgene in a prokaryotic host cell such as, but are not limited to, the β-lactamase promoter (Villa-Komaroff et al., Proc. Natl. Acad. Sci. USA 75:3727-3731 (1978)); the tac promoter (DeBoer et al., Proc. Natl. Acad. Sci. USA 80:21-25 (1983)); the T7 promoter, the T3 promoter, the M13 promoter or the M16 promoter; in a yeast host cell such as, but are not limited to, the GAL1, GAL4 or GAL10 promoter, the ADH (alcohol dehydrogenase) promoter, PGK (phosphoglycerol kinase) promoter, alkaline phosphatase promoter, glyceraldehyde-3-phosphate dehydrogenase III (TDH3) promoter, glyceraldehyde-3-phosphate dehydrogenase II (TDH2) promoter, glyceraldehyde-3-phosphate dehydrogenase I (TDH1) promoter, pyruvate kinase (PYK), enolase (ENO), or triose phosphate isomerase (TPI).

In some embodiments, the promoter may be a viral promoter, many of which are able to regulate expression of a transgene in several host cell types, including mammalian cells. Viral promoters that have been shown to drive constitutive expression of coding sequences in eukaryotic cells include, for example, simian virus promoters, herpes simplex virus promoters, papilloma virus promoters, adenovirus promoters, human immunodeficiency virus (HIV) promoters, Rous sarcoma virus promoters, cytomegalovirus (CMV) promoters, the long terminal repeats (LTRs) of Moloney murine leukemia virus and other retroviruses, the thymidine kinase promoter of herpes simplex virus as well as other viral promoters known to those of ordinary skill in the art.

In some embodiments, the gene control elements of an expression vector may also include 5' non-transcribing and 5' non-translating sequences involved with the initiation of transcription and translation, respectively, such as a TATA box, capping sequence, CAAT sequence, Kozak sequence and the like. Enhancer elements can optionally be used to increase expression levels of a polypeptide or protein to be expressed. Examples of enhancer elements that have been shown to function in mammalian cells include the SV40 early gene enhancer, as described in Dijkema et al., EMBO J. (1985) 4: 761 and the enhancer/promoter derived from the long terminal repeat (LTR) of the Rous Sarcoma Virus (RSV), as described in Gorman et al., Proc. Natl. Acad. Sci. USA (1982b) 79:6777 and human cytomegalovirus, as described in Boshart et al., Cell (1985) 41:521. Genetic control elements of an expression vector will also include 3' non-transcribing and 3' non-translating sequences involved with the termination of transcription and translation. Respectively, such as a poly polyadenylation (polyA) signal for stabilization and processing of the 3' end of an mRNA transcribed from the promoter. Poly A signals included, for example, the rabbit beta globin polyA signal, bovine growth hormone polyA signal, chicken beta globin terminator/polyA signal, or SV40 late polyA region.

Selectable Markers

Expression vectors will preferably but optionally include at least one selectable marker. In some embodiments, the selectable maker is a nucleic acid sequence encoding a resistance gene operably linked to one or more genetic regulatory elements, to bestow upon the host cell the ability to maintain viability when grown in the presence of a cytotoxic chemical and/or drug. In some embodiments, a selectable agent may be used to maintain retention of the expression vector within the host cell. In some embodiments, the selectable agent is may be used to prevent modification (i.e. methylation) and/or silencing of the transgene sequence within the expression vector. In some embodiments, a selectable agent is used to maintain episomal expression of the vector within the host cell. In some embodiments, the selectable agent is used to promote stable integration of the transgene sequence into the host cell genome. In some embodiments, an agent and/or resistance gene may include, but is not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), zeomycin, mycophenolic acid, or glutamine synthetase (GS, U.S. Pat. Nos. 5,122,464; 5,770,359; 5,827,739) for eukaryotic host cell; tetracycline, ampicillin, kanamycin or chloramphenicol for a prokaryotic host cell; and URA3, LEU2, HIS3, LYS2, HIS4, ADE8, CUP1 or TRP1 for a yeast host cell.

Expression vectors may be transfected, transformed or transduced into a host cell. As used herein, the terms "transfection," "transformation" and "transduction" all refer to the introduction of an exogenous nucleic acid sequence into a host cell. In some embodiments, expression vectors containing nucleic acid sequences encoding for I2S and/or FGE are transfected, transformed or transduced into a host cell at the same time. In some embodiments, expression vectors containing nucleic acid sequences encoding for I2S and/or FGE are transfected, transformed or transduced into a host cell sequentially. For example, a vector encoding an I2S protein may be transfected, transformed or transduced into a host cell first, followed by the transfection, transformation or transduction of a vector encoding an FGE protein, and vice versa. Examples of transformation, transfection and transduction methods, which are well known in the art, include liposome delivery, i.e., Lipofectamine™ (Gibco BRL) Method of Hawley-Nelson, Focus 15:73 (1193), electroporation, CaPO$_4$ delivery method of Graham and van der Erb, Virology, 52:456-457 (1978), DEAE-Dextran medicated delivery, microinjection, biolistic particle delivery, polybrene mediated delivery, cationic mediated lipid delivery, transduction, and viral infection, such as, e.g., retrovirus, lentivirus, adenovirus adeno-associated virus and Baculovirus (Insect cells). General aspects of cell host transformations have been described in the art, such as by Axel in U.S. Pat. No. 4,399, 216; Sambrook, supra, Chapters 1-4 and 16-18; Ausubel, supra, chapters 1, 9, 13, 15, and 16. For various techniques for transforming mammalian cells, see Keown et al., Methods in Enzymology (1989), Keown et al., Methods in Enzymology, 185:527-537 (1990), and Mansour et al., Nature, 336:348-352 (1988).

Once introduced inside cells, expression vectors may be integrated stably in the genome or exist as extra-chromosomal constructs. Vectors may also be amplified and multiple copies may exist or be integrated in the genome. In some embodiments, cells of the invention may contain 1, 2, 3, 4, 5, 6, 7, 8, 9, 10, 15, 20 or more copies of nucleic acids encoding an I2S protein. In some embodiments, cells of the invention may contain 1, 2, 3, 4, 5, 6, 7, 8, 9, 10, 15, or more copies of nucleic acids encoding an FGE protein. In some embodiments, cells of the invention may contain multiple copies (e.g., 2, 3, 4, 5, 6, 7, 8, 9, 10, 15, 20 or more) of nucleic acids encoding both I2S and FGE proteins.

Host Cells

As used herein, the term "host cells" refers to cells that can be used to produce recombinant I2S enzyme. In particular, host cells are suitable for producing recombinant I2S enzyme at a large scale. Suitable host cells can be derived from a variety of organisms, including, but not limited to, mammals, plants, birds (e.g., avian systems), insects, yeast, and bacteria. In some embodiments, host cells are mammalian cells. In some embodiments, a suitable host cell is not a endosomal acidification-deficient cell.

Mammalian Cell Lines

Any mammalian cell or cell type susceptible to cell culture, and to expression of polypeptides, may be utilized in accordance with the present invention as a host cell. Non-limiting examples of mammalian cells that may be used in accordance with the present invention include human embryonic kidney 293 cells (HEK293), HeLa cells; BALB/c mouse myeloma line (NSO/l, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells+/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci., 383:44-68 (1982)); MRC 5 cells; FS4 cells; and a human hepatoma line (Hep G2). In some embodiments, a suitable mammalian cell is not a endosomal acidification-deficient cell.

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

Non-Mammalian Cell Lines

Any non-mammalian derived cell or cell type susceptible to cell culture, and to expression of polypeptides, may be utilized in accordance with the present invention as a host cell. Non-limiting examples of non-mammalian host cells and cell lines that may be used in accordance with the present invention include cells and cell lines derived from *Pichia pastoris, Pichia methanolica, Pichia angusta, Schizosaccharomyces pombe, Saccharomyces cerevisiae,* and *Yarrowia lipolytica* for yeast; *Sodoptera frugiperda, Trichoplusis ni, Drosophila melanogaster* and *Manduca sexta* for insects; and *Escherichia coli, Salmonella typhimurium, Bacillus subtilis, Bacillus licheniformis, Bacteroides fragilis, Clostridia perfringens, Clostridia difficile* for bacteria; and *Xenopus Laevis* from amphibian.

Adaptable to Adherent vs Suspension Growth

In certain embodiments, a host cell is selected for generating a cell line based on certain preferable attributes or growth under particular conditions chosen for culturing cells. It will be appreciated by one skilled in the art, such attributes may be ascertained based on known characteristic and/or traits of an established line (i.e. a characterized commercially available cell line) or though empirical evaluation. In some embodiments, a cell line may be selected for its ability to grow on a feeder layer of cells. In some embodiments, a cell line may be selected for its ability to grow in suspension. In some embodiments, a cell line may be selected for its ability to grow as an adherent monolayer of cells. In some embodiments, such cells can be used with any tissue culture vessel or any vessel treated with a suitable adhesion substrate. In some embodiments, a suitable adhesion substrate is selected from the group consisting of collagen (e.g. collagen I, II, II, or IV), gelatin, fibronectin, laminin, vitronectin, fibrinogen, BD Matrigel™, basement membrane matrix, dermatan sulfate proteoglycan, Poly-D-Lysine and/or combinations thereof. In some embodiments, an adherent host cell may be selected and modified under specific growth conditions to grow in suspension. Such methods of modifying an adherent cell to grown in suspension are known in the art. For example, a cell may be conditioned to grow in suspension culture, by gradually removing animal serum from the growth media over time.

Cell Line Selection and Evaluation

According to the present invention, cells engineered to express recombinant I2S protein are selected for its ability to produce the recombinant I2S protein at commercially viable scale. In particular, engineered cells according to the present invention are able to produce recombinant I2S at a high level and/or with high enzymatic activity. In some embodiments, desirable cells, once cultivated under a cell culture condition (e.g., a standard large scale suspension or adherent culture condition), can produce I2S enzyme in an amount of or greater than about 5 picogram/cell/day (e.g., greater than about 10, 15, 20, 25, 30, 35, 40, 45, 50, 55, 60, 65, 70, 75, 80, 85, 90, 95, or 100 picogram/cell/day). In some embodiments, desired cells, once cultivated under a cell culture condition (e.g., a standard large scale suspension or adherent culture condition), are able to produce I2S enzyme in an amount ranging from about 5-100 picogram/cell/day (e.g., about 5-90 picogram/cell/day, about 5-80 picogram/cell/day, about 5-70 picogram/cell/day, about 5-60 picogram/cell/day, about 5-50 picogram/cell/day, about 5-40 picogram/cell/day, about 5-30 picogram/cell/day, about 10-90 picogram/cell/day, about 10-80 picogram/cell/day, about 10-70 picogram/cell/day, about 10-60 picogram/cell/day, about 10-50 picogram/cell/day, about 10-40 picogram/cell/day, about 10-30 picogram/cell/day, about 20-90 picogram/cell/day, about 20-80 picogram/cell/day, about 20-70 picogram/cell/day, about 20-60 picogram/cell/day, about 20-50 picogram/cell/day, about 20-40 picogram/cell/day, about 20-30 picogram/cell/day).

As discussed above, typically, the enzyme activity of I2S is influenced by a post-translational modification of a conserved cysteine (e.g., at amino acid 59) to formylglycine. This post-translational modification generally occurs in the endoplasmic reticulum during protein synthesis and is catalyzed by FGE. The enzyme activity of I2S is typically positively correlated with the extent to which the I2S has the formylglycine modification. For example, an I2S preparation that has a relatively high amount of formylglycine modification typically has a relatively high specific enzyme activity; whereas an I2S preparation that has a relatively low amount of formylglycine modification typically has a relatively low specific enzyme activity.

It is further contemplated that the ratio between the I2S and FGE protein or mRNA may also affect formylglycine modification on the produced recombinant I2S protein. In some embodiments, the I2S and FGE expressed in a desired cell have different protein and/or mRNA expression levels. In some embodiments, the I2S protein or mRNA expression level is at least 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8, 9, or 10-fold higher than the protein or mRNA level of FGE. In some embodiments the recombinant FGE protein or mRNA expression level is at least 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8, 9, or 10-fold higher than the protein or mRNA level of I2S.

In some embodiments, desirable cells, once cultivated under a cell culture condition (e.g., a standard large scale suspension or adherent culture condition), can produce I2S protein comprising at least about 50% (e.g., at least about 55%, 60%, 65%, 70%, 75%, 80%, 85%, 90%, 95%, 96%, 97%, 98%, 99%, or 100%) conversion of the cysteine residue corresponding to Cys59 of SEQ ID NO:1 to Cα-formylglycine (FGly). In some embodiments, desirable cells, once cultivated under a cell culture condition (e.g., a standard large scale suspension or adherent culture condition), can produce I2S enzyme comprising at least about 50% (e.g., at least about 55%, 60%, 65%, 70%, 75%, 80%, 85%, 90%, 95%, 96%, 97%, 98%, 99%, or 100%) conversion of the cysteine residue corresponding to Cys59 of SEQ ID NO:1 to Cα-formylglycine (FGly) and in an amount of or greater than about 5 picogram/cell/day (e.g., greater than about 10, 15, 20, 25, 30, 35, 40, 45, 50, 55, 60, 65, 70, 75, 80, 85, 90, 95, or 100 picogram/cell/day).

FGly Conversion Percentage

Various methods are known and can be used to determine the FGly conversion percentage. Generally, the percentage of formylglycine conversion (% FG) can be calculated using the following formula:

$$\% \ FG \ (of \ DS) = \frac{\text{Number of active I2S molecules}}{\text{Number of total (active + inactive) I2S molecules}} \times 100$$

For example 50% FG means half of the purified recombinant I2S is enzymatically inactive without any therapeutic effect. Various methods may be used to calculate % FG. For example, peptide mapping may be used. Briefly, an I2S protein may be digested into short peptides using a protease (e.g., trypsin or chymotrypsin). Short peptides may be separated and characterized using chromatography (e.g., HPLC) such that the nature and quantity of each peptide (in particular the peptide containing the position corresponding to position 59 of the mature human I2S) may be determined, as compared to a control (e.g., an I2S protein without FGly conversion or an I2S protein with 100% FGly conversion). The amount of peptides containing FGly (corresponding to number of active I2S molecules) and the total amount of peptides with both FGly and Cys (corresponding to number of total I2S molecules) may be determined and the ratio reflecting % FG calculated.

Specific Activity

As discussed above, typically, the enzyme activity of I2S is influenced by a post-translational modification of a conserved cysteine (e.g., at amino acid 59) to formylglycine. Thus, the enzyme activity of I2S is typically positively correlated with the extent to which the I2S has the formylglycine modification. For example, an I2S preparation that has a relatively high amount of formylglycine modification typically has a relatively high specific enzyme activity; whereas an I2S preparation that has a relatively low amount of formylglycine modification typically has a relatively low specific enzyme activity.

As can be appreciated by one skilled in the art, the enzymatic activity of recombinant I2S protein produced by cells of the present invention may be measured by various in vitro and in vivo assays. In some embodiments, a desired enzymatic activity, as measured by in vitro sulfate release activity assay using heparin disaccharide as substrate, of the produced recombinant I2S protein is at least about 20 U/mg, 30 U/mg, 40 U/mg, 50 U/mg, 60 U/mg, 70 U/mg, 80 U/mg, 90 U/mg, or 100 U/mg. In some embodiments, a desired enzymatic activity, as measured by in vitro sulfate release activity assay using heparin disaccharide as substrate, of the produced recombinant I2S protein ranges from about 20-100 U/mg (e.g., about 20-90 U/mg, about 20-80 U/mg, about 20-70 U/mg, about 20-60 U/mg, about 20-50 U/mg, about 20-40 U/mg, about 20-30 U/mg, about 30-100 U/mg, about 30-90 U/mg, about 30-80 U/mg, about 30-70 U/mg, about 30-60 U/mg, about 30-50 U/mg, about 30-40 U/mg, about 40-100 U/mg, about 40-90 U/mg, about 40-80 U/mg, about 40-70 U/mg, about 40-60 U/mg, about 40-50 U/mg). Exemplary conditions for performing in vitro sulfate release activity assay using heparin disaccharide as substrate are provided below. Typically, this assay measures the ability of I2S to release sulfate ions from a naturally derived substrate, heparin disaccharide. The released sulfate may be quantified by ion chromatography. In some cases, ion chromatography is equipped with a conductivity detector. As a non-limiting example, samples are first buffer exchanged to 10 mM Na acetate, pH 6 to remove inhibition by phosphate ions in the formulation buffer. Samples are then diluted to 0.075 mg/ml with reaction buffer (10 mM Na acetate, pH 4.4) and incubated for 2 hrs at 37° C. with heparin disaccharide at an enzyme to substrate ratio of 0.3 µg I2S/100 µg substrate in a 30 µL reaction volume. The reaction is then stopped by heating the samples at 100° C. for 3 min. The analysis is carried out using a Dionex IonPac AS18 analytical column with an IonPac AG18 guard column. An isocratic method is used with 30 mM potassium hydroxide at 1.0 mL/min for 15 minutes. The amount of sulfate released by the I2S sample is calculated from the linear regression analysis of sulfate standards in the range of 1.7 to 16.0 nmoles. The reportable value is expressed as Units per mg protein, where 1 unit is defined as 1 µmoles of sulfate released per hour and the protein concentration is determined by A280 measurements.

In some embodiments, the enzymatic activity of recombinant I2S protein produced by cells of the present invention may also be determined using various other methods known in the art such as, for example, 4-MUF assay which measures hydrolysis of 4-methylumbelliferyl-sulfate to sulfate and naturally fluorescent 4-methylumbelliferone (4-MUF). In some embodiments, a desired enzymatic activity, as measured by in vitro 4-MUF assay, of the produced recombinant I2S protein is at least about 2 U/mg, 4 U/mg, 6 U/mg, 8 U/mg, 10 U/mg, 12 U/mg, 14 U/mg, 16 U/mg, 18 U/mg, or 20 U/mg. In some embodiments, a desired enzymatic activity, as measured by in vitro 4-MUF assay, of the produced recombinant I2S protein ranges from about 0-50 U/mg (e.g., about 0-40 U/mg, about 0-30 U/mg, about 0-20 U/mg, about 0-10 U/mg, about 2-50 U/mg, about 2-40 U/mg, about 2-30 U/mg, about 2-20 U/mg, about 2-10 U/mg, about 4-50 U/mg, about 4-40 U/mg, about 4-30 U/mg, about 4-20 U/mg, about 4-10 U/mg, about 6-50 U/mg, about 6-40 U/mg, about 6-30 U/mg, about 6-20 U/mg, about 6-10 U/mg). Exemplary conditions for performing in vitro 4-MUF assay are provided below. Typically, a 4-MUF assay measures the ability of an I2S protein to hydrolyze 4-methylumbelliferyl-sulfate (4-MUF-SO$_4$) to sulfate and naturally fluorescent 4-methylumbelliferone (4-MUF). One milliunit of activity is defined as the quantity of enzyme required to convert one nanomole of 4-MUF-SO$_4$ to 4-MUF in one minute at 37° C. Typically, the mean fluorescence units (MFU) generated by I2S test samples with known activity can be used to generate a standard curve, which can be used to calculate the enzymatic activity of a sample of interest.

Cell Culture Medium and Condition

Various cell culture medium and conditions may be used to produce a recombinant I2S protein using engineered cells according to the present invention. For example, a recombinant I2S protein may be produced in serum-containing or serum-free medium. In some embodiments, a recombinant I2S protein is produced in serum-free medium. In some embodiments, a recombinant I2S protein is produced in an animal free medium, i.e., a medium that lacks animal-derived components. In some embodiments, a recombinant I2S protein is produced in a chemically defined medium. As used herein, the term "chemically-defined nutrient medium" refers to a medium of which substantially all of the chemical components are known. In some embodiments, a chemically defined nutrient medium is free of animal-derived components such as serum, serum derived proteins (e.g., albumin or fetuin), and other components. In some cases, a chemically-defined medium comprises one or more proteins (e.g., protein growth factors or cytokines) In some cases, a chemically-defined nutrient medium comprises one or more protein hydrolysates. In other cases, a chemically-defined nutrient medium is a protein-free media, i.e., a serum-free media that contains no proteins, hydrolysates or components of unknown composition.

In some embodiments, a chemically defined medium may be supplemented by one or more animal derived components. Such animal derived components include, but are not limited to, fetal calf serum, horse serum, goat serum, donkey serum, human serum, and serum derived proteins such as albumins (e.g., bovine serum albumin or human serum albumin).

Various cell culture conditions may be used to produce recombinant I2S proteins at large scale including, but not limited to, roller bottle cultures, bioreactor batch cultures and bioreactor fed-batch cultures. In some embodiments, recombinant I2S protein is produced by cells cultured in suspension. In some embodiments, recombinant I2S protein is produced by adherent cells.

Exemplary cell media and culture conditions are described in the Examples sections. Additional exemplary methods and compositions for producing recombinant I2S protein are described in the provisional application entitled "Methods and Compositions for Producing Recombinant Iduronate-2-Sulfatase" filed herewith on even date, the entire disclosure of which is hereby incorporated by reference.

Purification of Expressed I2S Protein

Various methods may be used to purify or isolate I2S protein produced according to various methods described herein. In some embodiments, the expressed I2S protein is secreted into the medium and thus cells and other solids may be removed, as by centrifugation or filtering for example, as a first step in the purification process. Alternatively or additionally, the expressed I2S protein is bound to the surface of the host cell. In this embodiment, the host cells expressing the polypeptide or protein are lysed for purification. Lysis of mammalian host cells can be achieved by any number of means well known to those of ordinary skill in the art, including physical disruption by glass beads and exposure to high pH conditions.

The I2S protein may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Protease inhibitors are particularly desired when cells must be lysed in order to isolate and purify the expressed polypeptide or protein.

Exemplary purification methods are described in the Examples sections below. Additional purification methods are described in the provisional application entitled "Purification of Recombinant I2S Protein" filed on herewith on even date, the entire disclosure of which is hereby incorporated by reference.

Pharmaceutical Composition and Administration

Purified recombinant I2S protein may be administered to a Hunter Syndrome patient in accordance with known methods. For example, purified recombinant I2S protein may be delivered intravenously, subcutaneously, intramuscularly, parenterally, transdermally, or transmucosally (e.g., orally or nasally)).

In some embodiments, a recombinant I2S or a pharmaceutical composition containing the same is administered to a subject by intravenous administration.

In some embodiments, a recombinant I2S or a pharmaceutical composition containing the same is administered to a subject by intrathecal administration. As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

In some embodiments, a recombinant I2S or a pharmaceutical composition containing the same is administered to the subject by subcutaneous (i.e., beneath the skin) administration. For such purposes, the formulation may be injected using a syringe. However, other devices for administration of the formulation are available such as injection devices (e.g., the Inject-Ease™ and Genject™ devices); injector pens (such as the GenPen™); needleless devices (e.g., MediJector™ and BioJector™); and subcutaneous patch delivery systems.

In some embodiments, intrathecal administration may be used in conjunction with other routes of administration (e.g., intravenous, subcutaneously, intramuscularly, parenterally, transdermally, or transmucosally (e.g., orally or nasally)).

The present invention contemplates single as well as multiple administrations of a therapeutically effective amount of a recombinant I2S or a pharmaceutical composition containing the same described herein. A recombinant I2S or a pharmaceutical composition containing the same can be administered at regular intervals, depending on the nature, severity and extent of the subject's condition (e.g., a lysosomal storage disease). In some embodiments, a therapeutically effective amount of a recombinant I2S or a pharmaceutical composition containing the same may be administered periodically at regular intervals (e.g., once every year, once every six months, once every five months, once every three months, bimonthly (once every two months), monthly (once every month), biweekly (once every two weeks), weekly, daily or continuously).

A recombinant I2S or a pharmaceutical composition containing the same can be formulated with a physiologically acceptable carrier or excipient to prepare a pharmaceutical composition. The carrier and therapeutic agent can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In some embodiments, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Additional exemplary pharmaceutical compositions and administration methods are described in PCT Publication WO2011/163649 entitled "Methods and Compositions for CNS Delivery of Iduronate-2-Sulfatase;" and provisional application Ser. No. 61/618,638 entitled "Subcutaneous administration of iduronate 2 sulfatase" filed on Mar. 30, 2012, the entire disclosures of both of which are hereby incorporated by reference.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

EXAMPLES

Example 1

Generation of Optimized Cell Line Co-expressing recombinant I2S and FGE

This example illustrates an exemplary optimized cell line co-expressing recombinant I2S and FGE that can be used to produce recombinant I2S protein. It will be clear to one skilled in the art, that a number of alternative approaches, expression vectors and cloning techniques are available.

A typical mature form of human iduronate-2-sulfatase enzyme (I2S) is a 525-amino acid glycoprotein that undergoes extensive processing and post translational modification for enzyme activation, such as glycosylation and cysteine conversion to formylglycine (FIG. 1). In mammalian cells, conserved cysteine residues within the I2S (i.e., at amino acid 59) enzyme are converted to formylglycine by the formylglycine generating enzyme (FGE). The conversion of cysteine to formylglycine within the active site of the I2S enzyme is an important step in generating the active form of the human sulfatase enzyme. The purpose of this experiment was to engineer an optimized human cell line co-expressing I2S and FGE for generating active recombinant I2S.

FIG. 2 illustrates a number of exemplary construct designs for co-expression of I2S and FGE. For example, expression units of I2S and FGE can be located on separate vectors and the separate vectors can be co-transfected or transfected separately (FIG. 2A). Alternatively, expression units of I2S and FGE can be located on the same vector (FIG. 2B). In one configuration, I2S and FGE can be on the same vector but under the control of separate promoters, also referred to as separate cistrons (FIG. 2B(1)). Alternatively, I2S and FGE can be designed as transcriptionally linked cistrons, that is, I2S and FGE are designed as one open reading frame under the control of a same promoter (FIG. 2B(2)). Typically, an internal ribosome entry site (IRES) is designed to allow cap independent translation initiation of the messenger RNA (FIG. 2B(2)).

A human cell line was engineered to co-express human I2S protein with the amino acid sequence shown in SEQ ID NO:2 and human formylglycine generating enzyme (FGE) with the amino acid sequence shown in SEQ ID NO:6.

SEQ ID NO: 2
> Full-length Precursor iduronate 2-sulfatase
MPPPRTGRGLLWLGLVLSSVCVALGSETQANSTTDALNVLLIIVDDLRPSLGCYGDKLV

RSPNIDQLASHSLLFQNAFAQQAVCAPSRVSFLTGRRPDTTRLYDFNSYWRVHAGNFSTI

PQYFKENGYVTMSVGKVFHPGISSNHTDDSPYSWSFPPYHPSSEKYENTKTCRGPDGEL

HANLLCPVDVLDVPEGTLPDKQSTEQAIQLLEKMKTSASPFFLAVGYHKPHIPFRYPKEF

QKLYPLENITLAPDPEVPDGLPPVAYNPWMDIRQREDVQALNISVPYGPIPVDFQRKIRQ

SYFASVSYLDTQVGRLLSALDDLQLANSTIIAFTSDHGWALGEHGEWAKYSNFDVATH

VPLIFYVPGRTASLPEAGEKLFPYLDPFDSASQLMEPGRQSMDLVELVSLFPTLAGLAGL

QVPPRCPVPSFHVELCREGKNLLKHFRFRDLEEDPYLPGNPRELIAYSQYPRPSDIPQWN

SDKPSLKDIKIMGYSIRTIDYRYTVWVGFNPDEFLANFSDIHAGELYFVDSDPLQDHNMY

NDSQGGDLFQLLMP

SEQ ID NO: 6
Full-length human FGE precursor:
MAAPALGLVCGRCPELGLVLLLLLSLLCGAAGSQEAGTGAGAGSLAGSCGCGTPQRP

GAHGSSAAAHRYSREANAPGPVPGERQLAHSKMVPIPAGVFTMGTDDPQIKQDGEAPA

RRVTIDAFYMDAYEVSNTEFEKFVNSTGYLTEAEKFGDSFVFEGMLSEQVKTNIQQAVA

AAPWWLPVKGANWRHPEGPDSTILHRPDHPVLHVSWNDAVAYCTWAGKRLPTEAEW

EYSCRGGLHNRLFPWGNKLQPKGQHYANIWQGEFPVTNTGEDGFQGTAPVDAFPPNGY

GLYNIVGNAWEWTSDWWTVHHSVEETLNPKGPPSGKDRVKKGGSYMCHRSYCYRYR

CAARSQNTPDSSASNLGFRCAADRLPTMD

To generate an I2S expressing cell line, cells were stably transfected with a codon optimized nucleic acid sequence (SEQ ID NO. 7) encoding an I2S protein with the amino acid sequence shown in SEQ ID NO:2 and a nucleic acid sequence (SEQ ID NO. 8) encoding the human FGE enzyme as set forth in SEQ ID NO. 6.

```
                                                    SEQ ID NO: 7
> Homo sapiens codon optimized iduronate 2-sulfatase (IDS),
transcript variant 1, mRNA
ATGCCCCCGCCCCGCACCGGCCGCGGCCTGCTGTGGCTGGGCCTGGTGCTGAGCAGCGTGTGCGTGGC

CCTGGGCAGCGAGACCCAGGCCAACAGCACCACCGACGCCCTGAACGTGCTGCTGATCATCGTGGAC

GACCTGCGCCCCAGCCTGGGCTGCTACGGCGACAAGCTGGTGCGCAGCCCCAACATCGACCAGCTGGC

CAGCCACAGCCTGCTGTTCCAGAACGCCTTCGCCCAGCAGGCCGTGTGCGCCCCCAGCCGCGTGAGCT

TCCTGACCGGCCGCCGCCCCGACACCACCCGCCTGTACGACTTCAACAGCTACTGGCGCGTGCACGCC

GGCAACTTCAGCACCATCCCCCAGTACTTCAAGGAGAACGGCTACGTGACCATGAGCGTGGGCAAGGT

GTTCCACCCCGGCATCAGCAGCAACCACACCGACGACAGCCCCTACAGCTGGAGCTTCCCCCCCTACC

ACCCCAGCAGCGAGAAGTACGAGAACACCAAGACCTGCCGCGGCCCCGACGGCGAGCTGCACGCCAA

CCTGCTGTGCCCCGTGGACGTGCTGGACGTGCCCGAGGGCACCCTGCCCGACAAGCAGAGCACCGAGC

AGGCCATCCAGCTGCTGGAGAAGATGAAGACCAGCGCCAGCCCCTTCTTCCTGGCCGTGGGCTACCAC

AAGCCCCACATCCCCTTCCGCTACCCCAAGGAGTTCCAGAAGCTGTACCCCCTGGAGAACATCACCCT

GGCCCCCGACCCCGAGGTGCCCGACGGCCTGCCCCCCGTGGCCTACAACCCCTGGATGGACATCCGCC

AGCGCGAGGACGTGCAGGCCCTGAACATCAGCGTGCCCTACGGCCCCATCCCCGTGGACTTCCAGCGC

AAGATCCGCCAGAGCTACTTCGCCAGCGTGAGCTACCTGGACACCCAGGTGGGCCGCCTGCTGAGCGC

CCTGGACGACCTGCAGCTGGCCAACAGCACCATCATCGCCTTCACCAGCGACCACGGCTGGGCCCTGG

GCGAGCACGGCGAGTGGGCCAAGTACAGCAACTTCGACGTGGCCACCCACGTGCCCCTGATCTTCTAC

GTGCCCGGCCGCACCGCCAGCCTGCCCGAGGCCGGCGAGAAGCTGTTCCCCTACCTGGACCCCTTCGA

CAGCGCCAGCCAGCTGATGGAGCCCGGCCGCCAGAGCATGGACCTGGTGGAGCTGGTGAGCCTGTTCC

CCACCCTGGCCGGCCTGGCCGGCCTGCAGGTGCCCCCCCGCTGCCCCGTGCCCAGCTTCCACGTGGAG
```

```
                                            -continued
CTGTGCCGCGAGGGCAAGAACCTGCTGAAGCACTTCCGCTTCCGCGACCTGGAGGAGGACCCCTACCT

GCCCGGCAACCCCCGCGAGCTGATCGCCTACAGCCAGTACCCCCGCCCCAGCGACATCCCCCAGTGGA

ACAGCGACAAGCCCAGCCTGAAGGACATCAAGATCATGGGCTACAGCATCCGCACCATCGACTACCG

CTACACCGTGTGGGTGGGCTTCAACCCCGACGAGTTCCTGGCCAACTTCAGCGACATCCACGCCGGCG

AGCTGTACTTCGTGGACAGCGACCCCCTGCAGGACCACAACATGTACAACGACAGCCAGGGCGGCGA

CCTGTTCCAGCTGCTGATGCCCTAG

SEQ ID NO: 8
> Homo sapiens Full-length Precursor formylglycine generating
enzyme (FGE), mRNA
ATGGCTGCGCCCGCACTAGGGCTGGTGTGTGGACGTTGCCCTGAGCTGGGTCTCGTCCTCTTGCTGCTG

CTGCTCTCGCTGCTGTGTGGAGCGGCAGGGAGCCAGGAGGCCGGGACCGGTGCGGGCGCGGGGTCCC

TTGCGGGTTCTTGCGGCTGCGGCACGCCCAGCGGCCTGGCGCCCATGGCAGTTCGGCAGCCGCTCAC

CGATACTCGCGGGAGGCTAACGCTCCGGGCCCCGTACCCGGAGAGCGGCAACTCGCGCACTCAAAGA

TGGTCCCCATCCCTGCTGGAGTATTTACAATGGGCACAGATGATCCTCAGATAAAGCAGGATGGGGAA

GCACCTGCGAGGAGAGTTACTATTGATGCCTTTTACATGGATGCCTATGAAGTCAGTAATACTGAATTT

GAGAAGTTTGTGAACTCAACTGGCTATTTGACAGAGGCTGAGAAGTTGGCGACTCCTTTGTCTTTGAA

GGCATGTTGAGTGAGCAAGTGAAGACCAATATTCAACAGGCAGTTGCAGCTGCTCCCTGGTGGTTACC

TGTGAAAGGCGCTAACTGGAGACACCCAGAAGGGCCTGACTCTACTATTCTGCACAGGCCGGATCATC

CAGTTCTCCATGTGTCCTGGAATGATGCGGTTGCCTACTGCACTTGGGCAGGGAAGCGGCTGCCCACG

GAAGCTGAGTGGGAATACAGCTGTCGAGGAGGCCTGCATAATAGACTTTTCCCCTGGGGCAACAAACT

GCAGCCCAAAGGCCAGCATTATGCCAACATTTGGCAGGGCGAGTTTCCGGTGACCAACACTGGTGAGG

ATGGCTTCCAAGGAACTGCGCCTGTTGATGCCTTCCCTCCCAATGGTTATGGCTTATACAACATAGTGG

GGAACGCATGGGAATGGACTTCAGACTGGTGGACTGTTCATCATTCTGTTGAAGAAACGCTTAACCCA

AAAGGTCCCCCTTCTGGGAAAGACCGAGTGAAGAAAGGTGGATCCTACATGTGCCATAGGTCTTATTG

TTACAGGTATCGCTGTGCTGCTCGGAGCCAGAACACACCTGATAGCTCTGCTTCGAATCTGGGATTCCG

CTGTGCAGCCGACCGCCTGCCCACCATGGACTGA
```

Both I2S- and FGE-encoding nucleic acid sequences are controlled by a human CMV promoter. Translation of I2S mRNA results in synthesis of a 550 amino acid full length I2S protein (SEQ ID NO:2), which includes a 25 amino acid signal peptide. The signal peptide is removed and a soluble enzyme is secreted from the cell.

The bacterial neomycin phosphotransferase (neo) coding sequence and/or Blasticidin S Deaminase (BSD) gene were used to allow for selection of transfected cells using the neomycin analog G418 and/or blasticidin, respectively. In addition, the mouse dihydrofolate reductase (DHFR) gene was used on the I2S- and/or FGE-encoding vector(s) to allow for isolation of cell lines containing increased copies of the I2S- and/or FGE-encoding sequences by methotrexate (MTX) selection.

Cells producing I2S were isolated and subjected to appropriate drug selection to isolate cells with an increased number of copies of the transfected I2S and/or FGE genes. Quantification of I2S was performed by ELISA.

The cell population was also subjected to step-wise selection in methotrexate (MTX) to isolate cells with increased I2S productivity. I2S productivity was monitored during MTX selection by ELISA.

After several rounds of propagation, several I2S producing clones were then subjected to suspension adaptation in serum-free media through a stepwise reduction from DMEM containing 10% calf serum to serum free chemically defined media. Several individual clonal populations were established through limited dilution cloning. Colonies were screened by I2S enzyme activity assay and ELISA. Two stable cell lines 2D and 4D showed high percent viability and robust expression of I2S and were selected for further development.

Example 2

Evaluation of Stable Cell Lines Co-Expressing I2S and FGE

Additional experiments were carried out to characterize two cell lines 2D and 4D co-expressing I2S and FGE.

Specific Activity

First specific activity of the I2S enzyme was evaluated. I2S enzyme produced from the 2D and 4D cell lines were analyzed for specific activity using a fluorescence based 4-MUF assay. Briefly, the assay measures the hydrolysis of I2S substrate 4-methylumbelliferyl-sulfate (4-MUF-SO$_4$). Upon cleavage of the 4-MUF-SO$_4$ substrate by I2S, the molecule is converted to sulfate and naturally fluorescent 4-methylumbelliferone (4-MUF). As a result, I2S enzyme activity can be determined by evaluating the overall change in fluorescent signal over time. For this experiment, purified I2S enzyme produced from the I2S-AF 2D and 4D human cell lines were incubated with a solution of 4-methylumbelliferyl-sulfate (4-MUF-SO$_4$), Potassium Salt, Sigma Cat. # M-7133). Calibration of the assay was performed using a series of control reference samples, using commercially available I2S enzyme diluted at 1:100, 1:200 and 1:20,000 of the stock solution. The enzymatic assay was run at 37° C. and assayed using a calibrated fluorometer. Using the fluorescence values obtained for each reference standard, the percent coefficient of variation was determined using the following equation:

$$\% \ CV = \frac{\text{Standard Deviation of Raw Fluorescence Values}(N=3)}{\text{Average Fluorescence Value}} \times 100\%$$

The percent CV values were then used to calculate the Corrected Average Fluorescence for each sample, in order to determine the reportable enzyme activity, expressed in mU/mL using the following formula:

$$mU/mL = (CFU)\left(\frac{1 \ \text{nmole/L}}{10 \ FU}\right)\left(\frac{1 \ L}{10^3 \ mL}\right)\left(\frac{2.11 \ mL}{0.01 \ mL}\right)\left(\frac{1 \ \text{hour}}{60 \ \text{min}}\right)\left(\frac{1 \ mU}{\text{nmole}}\right)(DF)$$

CFU=Negative corrected average fluorescence
DF—Dilution Factor

One milliunit of activity is the quantity of enzyme required to convert 1 nanomole of 4-methylumbelliferyl-sulfate to 4-methylumbelliferone in 1 minute at 37° C.

Percent Formylglycine Conversion

Peptide mapping can be used to determine Percent FGly conversion. I2S activation requires Cysteine (corresponding to position 59 of mature human I2S) to formylglycine conversion by formylglycine generating enzyme (FGE) as shown below:

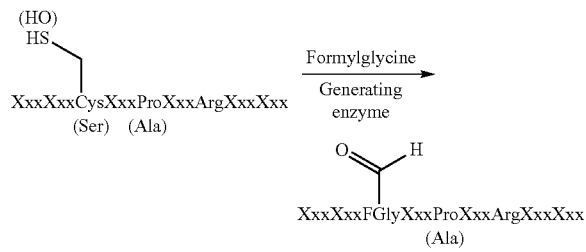

Therefore, the percentage of formylglycine conversion (% FG) can be calculated using the following formula:

$$\% \ FG \ (\text{of} \ DS) = \frac{\text{Number of active 12S molecules}}{\text{Number of total (active + inactive)12S molecules}} \times 100$$

For example 50% FG means half of the purified recombinant I2S is enzymatically inactive without any therapeutic effect.

Peptide mapping was used to calculate % FG. Briefly, a recombinant I2S protein was digested into short peptides using a protease (e.g., trypsin or chymotrypsin). Short peptides were separated and characterized using HPLC. The peptide containing the position corresponding to position 59 of the mature human I2S was characterized to determine if the Cys at position 59 was converted to a FGly as compared to a control (e.g., an I2S protein without FGly conversion or an I2S protein with 100% FGly conversion). The amount of peptides containing FGly (corresponding to number of active I2S molecules) and the total amount of peptides with both FGly and Cys (corresponding to number of total I2S molecules) may be determined based on the corresponding peak areas and the ratio reflecting % FG was calculated.

Correlation between Percentage FGly Conversion and Specific Activity

Exemplary correlation between percentage FGly conversion and specific activity is shown in FIG. 3. As can be seen, the data suggest that a higher percentage of formylglycine conversion results in higher I2S enzyme activity.

Glycan Map

Figure 4:
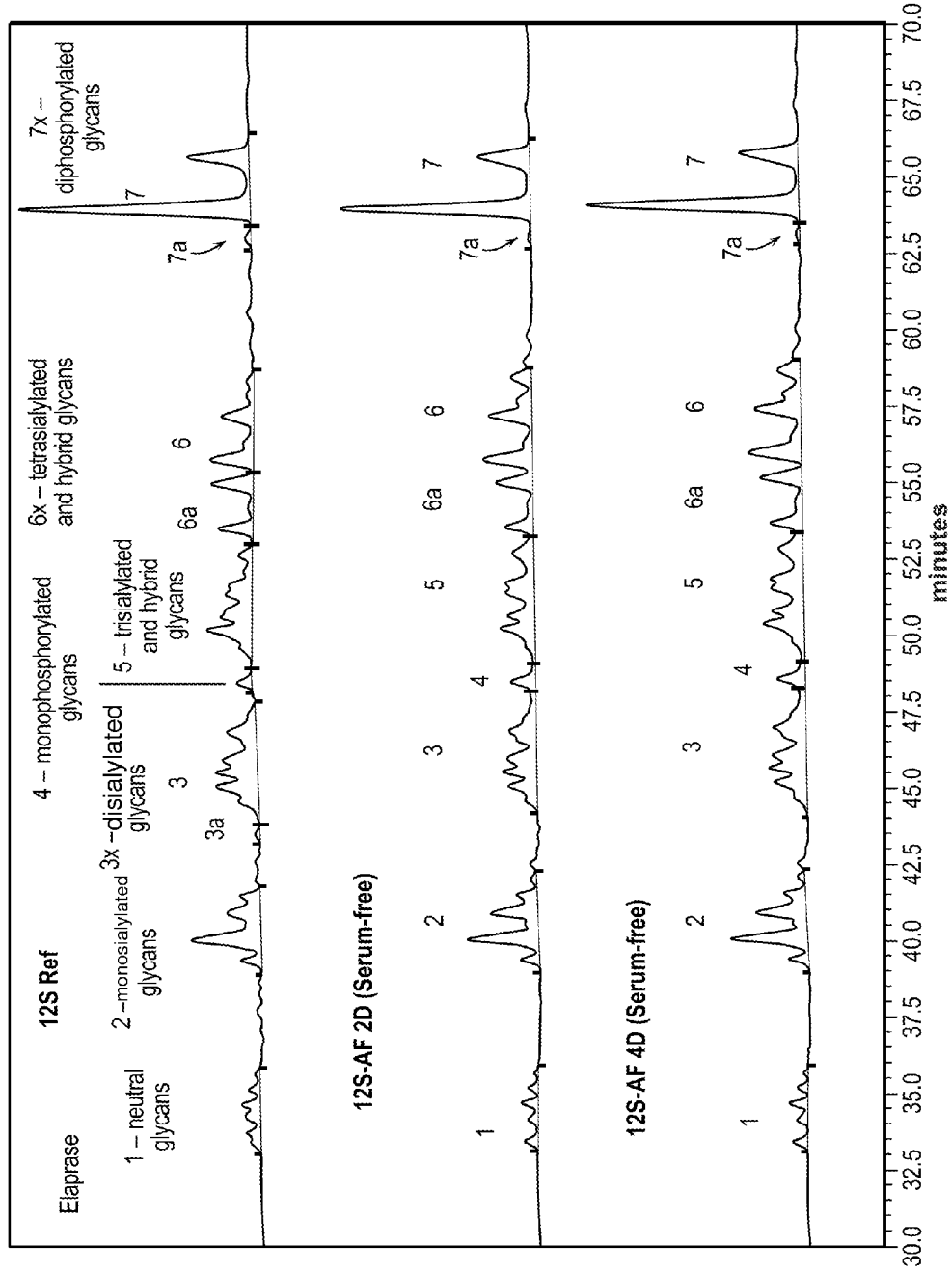
FIG. 4 depicts an exemplary glycan profile generated for recombinant I2S enzyme produced using the I2S-AF 2D and 4D cell lines grown under serum-free cell culture conditions as compared to a reference recombinant I2S enzyme.

The glycan composition of recombinant I2S protein produced by cell line 2D and 4D was determined. Quantification of the glycan composition was performed, using anion exchange chromatography. As described below, the glycan map of recombinant I2S generated under these conditions consists of seven peak groups, eluting according to an increasing amount of negative charges, at least partly derived from sialic acid and mannose-6-phosphate glycoforms resulting from enzymatic digest. Briefly, purified recombinant I2S obtained using the serum-free cell culture method (I2S-AF 2D Serum-free and I2S-AF 4D Serum-free) and reference recombinant I2S produced, were treated with either (1) purified neuraminidase enzyme (isolated from *Arthrobacter Ureafaciens* (10 mU/µL), Roche Biochemical (Indianapolis, Ind.), Cat. #269 611 (1U/100 µL)) for the removal of sialic acid residues, (2) alkaline phosphatase for 2 hours at 37±1° C. for complete release of mannose-6-phosphate residues, (3) alkaline phosphatase+neuraminidase, or (4) no treatment. Each enzymatic digest was analyzed by High Performance Anion Exchange Chromatography with Pulsed Amperometric Detection (HPAE-PAD) using a CarboPac PA1 Analytical Column equipped with a Dionex CarboPac PA1 Guard Column. A series of sialic acid and mannose-6-phosphate standards in the range of 0.4 to 2.0 nmoles were run for each assay. An isocratic method using 48 mM sodium acetate in 100 mM sodium hydroxide was run for a minimum of 15 minutes at a flow rate of 1.0 mL/min at ambient column temperature to elute each peak. The data generated from each individual run, for both the I2S-AF and reference I2S samples, were each combined into a single chromatograph to represent the glycan map for each respective recombinant protein. As indicated in FIG. 4, an exemplary glycan map for I2S produced by cell line 2D and 4D displayed representative elution peaks (in the order of elution) constituting neutrals, monosialylated, disialylated, monophosphorylated, trisialylated and hybrid (monosialylated and capped mannose-6-phosphate), tetrasialylated and hybrid (disialylated and capped mannose-6-phosphate) and diphosphorylated glycans.

Example 3

Serum-Free Suspension Cell Culture

This example demonstrates that a large scale serum free suspension culture may be developed to cultivate an optimized cell line to produce recombinant I2S.

Serum Free Suspension Cell Culture System

Briefly, a seed culture was established using the 2D or 4D cell line of Example 1. Cells were transferred to a 250 mL tissue culture shake flask containing serum-free chemically defined expansion medium supplemented with MTX for selection, adjusted with sodium bicarbonate to a pH of 7.3 and grown at 37° C. at 5% $CO_2$ for several days. Once the culture reached a sufficient cell density and viability, the initial seed culture was used to inoculate the first of a series of step-wise cell culture expansions in 500 mL tissue culture shake flasks followed by 1 L tissue culture shake flasks.

A batch culture expansion was performed by transferring each of the 1 L cultures into a 10 L Cellbag Bioreactor® (Wave Europe), and adding expansion medium. After reaching a sufficient cell density, new expansion medium was added and the cells grown to a sufficient density. The 10 L Cellbag was transferred to a Wave Bioreactor® system (Wave Europe) and culture conditions were modified to allow for growth under continuous medium perfusion. Expansion growth medium was delivered and samples were collected for off-line metabolite analysis of pH, glutamine, glutamate, glucose, ammonium, lactate, $pCO_2$ and osmolarity.

Upon reaching a sufficient cell density, the entire 10 L cell culture was transferred to a 50 L Wave Cellbag Bioreactor®, containing fresh expansion medium, and grown to a sufficient cell density using a Wave Bioreactor® system.

Cell expansion was next performed using a 200 L disposable bioreactor and centrifuge perfusion device (Centritech® CELL II unit, Pneumatic Scale Corporation), which was designed to concentrate cells and clarify media for recycling during perfusion mediated cell culture. Expansion medium (adjusted to pH 7.10) was inoculated with a portion of the 50 L culture and grown to a sufficient cell density.

Next a portion of the 200 L culture was used to seed a 2000 L disposable bioreactor and centrifuge perfusion device (Centritech® CELL II unit, Pneumatic Scale Corporation) in production medium (adjusted to pH 7.20). Cells were grown under batch growth conditions. Following the two day growth, conditions were adjusted for continuous perfusion, until a transition phase was reached. Cells were grown under perfusion growth conditions for the 24 hour transition phase.

For the production phase, two Centritech CELL II units were used. Production phase was started approximately 24 hours after the start of the transition phase and maintained for a desired period, by regulating the bleed rate.

While certain compounds, compositions and methods described herein have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. A cell comprising
a first nucleic acid encoding an iduronate-2-sulfatase (I2S) protein comprising an amino acid sequence at least 90% identical to SEQ ID NO:1; and
a second nucleic acid encoding a formylglycine generating enzyme (FGE) protein comprising an amino acid sequence at least 90% identical to SEQ ID NO:5,
wherein the first and/or the second nucleic acid are exogenous and wherein the cell, once cultivated under a cell culture condition, produces I2S protein comprising at least about 70% conversion of the cysteine residue corresponding to Cys59 of SEQ ID NO:1 to Cα-formylglycine (FGly), and wherein the level of iduronate-2-sulfatase protein expressed by the cell is between 0.3-fold and 10-fold higher than the level of formylglycine generating enzyme protein expressed by the cell.

2. A cell comprising
a first nucleic acid encoding an iduronate-2-sulfatase (I2S) protein comprising an amino acid sequence at least 90% identical to SEQ ID NO:1; and
a second nucleic acid encoding a formylglycine generating enzyme (FGE) protein comprising an amino acid sequence at least 90% identical to SEQ ID NO:5,
wherein the first and/or the second nucleic acid are exogenous and wherein the cell, once cultivated under a cell culture condition, produces I2S protein comprising at least about 70% conversion of the cysteine residue corresponding to Cys59 of SEQ ID NO:1 to Cα-formylglycine (FGly) and at a specific productivity rate of greater than about 30 picogram/cell/day.

3. The cell of claim 1, wherein the cell, once cultivated under a cell culture condition, produces the I2S protein comprising at least about 80% conversion of the cysteine residue corresponding to Cys59 of SEQ ID NO:1 to Cα-formylglycine (FGly).

4. The cell of claim 1, wherein the cell, once cultivated under a cell culture condition, produces the I2S protein comprising at least about 90% conversion of the cysteine residue corresponding to Cys59 of SEQ ID NO:1 to Cα-formylglycine (FGly).

5. The cell of claim 1, wherein the cell, once cultivated under a cell culture condition, produces the I2S protein comprising at least about 95% conversion of the cysteine residue corresponding to Cys59 of SEQ ID NO:1 to Cα-formylglycine (FGly).

6. The cell of claim 1, wherein the cell, once cultivated under a cell culture condition, produces the I2S protein comprising at least about 97% conversion of the cysteine residue corresponding to Cys59 of SEQ ID NO:1 to Cα-formylglycine (FGly).

7. The cell of claim 1, wherein the first and/or the second nucleic acid is operably linked to a hCMV promoter.

8. The cell of claim 1, wherein the first nucleic acid comprises a sequence at least 70% identical to SEQ ID NO:7.

9. The cell of claim 1, wherein the second nucleic acid comprises a sequence at least 70% identical to SEQ ID NO:8.

10. The cell of claim 1, wherein both of the first and second nucleic acids are exogenous.

11. The cell of claim 1, wherein the cell is a mammalian cell.

12. The cell of claim 11, wherein the mammalian cell is a CHO cell.

13. A method of producing recombinant iduronate-2-sulfatase (I2S) protein comprising cultivating a cell of claim 1 under conditions such that the recombinant I2S and FGE proteins are co-expressed in the cell.

14. The method of claim 13, wherein the cell is cultivated in a large scale bioreactor process at a scale selected from 10 L, 200 L, 500 L, 1000 L, 1500 L, or 2000 L.

15. The method of claim 14, wherein the bioreactor process is a perfusion process.

16. The method of claim 13, wherein the cell is cultivated in a serum-free medium.

17. The method of claim 13, wherein the cell is cultivated in suspension.

18. The method of claim 13, wherein the method further comprises a step of purifying the recombinant I2S protein.

19. The cell according to claim 1, wherein the first nucleic acid encodes an iduronate-2-sulfatase (I2S) protein comprising an amino acid sequence at least 95% identical to SEQ ID NO:1.

20. The cell according to claim 1, wherein the second nucleic acid encodes a formylglycine generating enzyme (FGE) protein comprising an amino acid sequence at least 95% identical to SEQ ID NO:5.

21. The cell according to claim 1, wherein the first nucleic acid encodes an iduronate-2-sulfatase (I2S) protein comprising an amino acid sequence identical to SEQ ID NO:1.

22. The cell according to claim 1, wherein the second nucleic acid encodes a formylglycine generating enzyme (FGE) protein comprising an amino acid sequence identical to SEQ ID NO:5.

* * * * *